(12) United States Patent
McCarthy et al.

(10) Patent No.: US 6,395,872 B1
(45) Date of Patent: May 28, 2002

(54) SECRETED NEURAL ADHESION PROTEINS

(75) Inventors: Sean Anthony McCarthy, Boston; David Paul Gearing, Welleslev; Douglas Adam Levinson, Sherborn, all of MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/991,326

(22) Filed: Nov. 21, 2001

Related U.S. Application Data

(62) Division of application No. 09/707,802, filed on Nov. 9, 2000, which is a continuation of application No. 09/283,503, filed on Apr. 1, 1999, now abandoned, which is a division of application No. 08/752,307, filed on Nov. 19, 1996, now Pat. No. 5,952,171.

(51) Int. Cl.$^7$ .......................... C07K 7/00; C07K 14/47
(52) U.S. Cl. ...................... 530/300; 530/324; 530/325; 530/326; 530/350
(58) Field of Search ................................ 530/300, 324, 530/325, 326, 350

(56) References Cited

FOREIGN PATENT DOCUMENTS

WO    WO 98/17795    *    4/1998

* cited by examiner

*Primary Examiner*—Terry McKelvey
(74) *Attorney, Agent, or Firm*—Millennium Pharmaceuticals, Inc.

(57) ABSTRACT

The invention features a method for identifying a cDNA nucleic acid encoding a mammalian protein having a signal sequence, which method includes the following steps: (a) providing library of mammalian cDNA; (b) ligating the library of mammalian cDNA to DNA encoding alkaline phosphatase lacking both a signal sequence and a membrane anchor sequence to form ligated DNA; 8 transforming bacterial cells with the ligated DNA to create a bacterial cell clone library; (d) isolating DNA comprising the mammalian cDNA from at least one clone in the bacterial cell clone library; (e) separately transfecting DNA isolated from clones in step (d) into mammalian cells which do not express alkaline phosphatase to create a mammalian cell clone library wherein each clone in the mammalian cell clone library corresponds to a clone in the bacterial cell clone library; (f) identifying a clone in the mammalian cell clone library which expresses alkaline phosphatase; (g) identifying the clone in the bacterial cell clone library corresponding to the clone in the mammalian cell clone library identified in step (f); and (h) isolating and sequencing a portion of the mammalian cDNA present in the bacterial cell library clone identified in step (g) to identify a mammalian cDNA encoding a mammalian protein having a signal sequence.

8 Claims, 10 Drawing Sheets ptrAP3 vector sequence

```
AAGCTTGGCTGTGGAATGTGTGTCAGTTAGGGTGTGGAAAGTCCCCAGGCTCCCCAGCAGGCAGA
AGTATGCAAAGCATGCATCTCAATTAGTCAGCAACCAGGTGTGGAAAGTCCCCAGGCTCCCCAGC
AGGCAGAAGTATGCAAAGCATGCATCTCAATTAGTCAGCAACCATAGTCCCGCCCCTAACTCCGC
CCATCCCGCCCCTAACTCCGCCCAGTTCCGCCCATTCTCCGCCCCATGGCTGACTAATTTTTTTT
ATTTATGCAGAGGCCGAGGCCGCCTCGGCCTCTGAGCTATTCCAGAAGTAGTGAGGAGGCTTTTT
TGGAGGCCTAGGCTTTTGCAAAAAGCTCCTCCGATCGAGGGGCTCGCATCTCTCCTTCACGCGCC
CGCCGCCCTACCTGAGGCCGCCATCCACGCCGGTTGAGTCGCGTTCTGCCGCCTCCCGCCTGTGG
TGCCTCCTGAACTGCGTCCGCCGTCTAGGTAAGTTTAAAGCTCAGGTCGAGACCGGGCCTTTGTC
CGGCGCTCCCTTGGAGCCTACCTAGACTCAGCCGGCTCTCCACGCTTTGCCTGACCCTGCTTGCT
CAACTCTACGTCTTTGTTTCGTTTCTGTTCTGCGCCGTTACAGATCCAAGCTCTGAAAACCAG
AAAGTTAACTGGTAAGTTTAGTCTTTTTGTCTTTTATTTCAGGTCCCAGGTCCCGGATCCGGTGA
TCCAAATCTAAGAACTGCTCCTCAGTGAGTGTTGCCTTTACTTCTAGGCCTGTACGAAGTGTTA
CTTCTGCTCTAAAAGCTGCGGAATTCGCACCACCGTAGTTTTTACGCCCGGTGAGCGCTCCACCC
GCACCTACAAGCGCGTGTATGATGAGGTGTACGGCGACGAGGACCTGCTTGAGCAGGCCAACGAG
CGCCTCGGGGAGTTTGCCTACGAAAGCGGCATAAGGACATGTTGGCGTTGCCGCTGGACGAGGG
CAACCCAACACCTAGCCTAAAGCCCGTGACACTGCAGCAGGTGCTGCCCACGCTTGCACCGTCCG
AAGAAAAGCGGCCTAAAGCGCGAGTCTGGTGACTTGGCACCCACCGTGCAGCTGATGGTACCC
AAGCGCCAGCGACTGGAAGATGTCTTGGAAAAAATGACCGTGGAGCCTGGGCTGGAGCCCGAGGT
CCGCGTGCGGCCAATCAAGCAGGTGGCACCGGGACTGGGCGTGCAGACCGTGGACGTTCAGATAC
CCACCACCAGTAGCACTAGTATTGCCACTGCCACAGAGGGCATGGAGACACAAACGTCCCCGGTT
GCCTAGCTCGAGATCATCCCAGTTGAGGAGGAGAACCCGGACTTCTGGAACCGCGAGGCAGCCGA
GGCCCTGGGTGCCGCCAAGAAGCTGCAGCCTGCACAGACAGCCGCCAAGAACCTCATCATCTTCC
TGGGCGATGGGATGGGGGTGTCTACGGTGACAGCGGCCAGGATCCTAAAAGGGCAGAAGAAGGAC
AAACTGGGGCCTGAGATACCCCTGGCCATGGACCGCTTCCCATATGTGGCTCTGTCCAAGACATA
CAATGTAGACAAACATGTGCCAGACAGTGGAGCCACAGCCACGGCCTACCTGTGCGGGGTCAAGG
GCAACTTCCAGACCATTGGCTTGAGTGCAGCCGCCGCTTTAACCAGTGCAACACGACACGCGGC
AACGAGGTCATCTCCGTGATGAATCGGGCCAAGAAAGCAGGGAAGTCAGTGGGAGTGGTAACCAC
CACACGAGTGCAGCACGCCTCGCCAGCCGGCACCTACGCCCACGGTGAACCGCAACTGGTACT
CGGACGCCGACGTGCCTGCCTCGGCCCGCCAGGAGGGGTGCCAGGACATCGCTACGCAGCTCATC
TCCAACATGGACATTGACGTGATCCTAGGTGGAGGCCGAAAGTACATGTTTCGCATGGGAACCCC
AGACCCTGAGTACCCAGATGACTACAGCCAAGGTGGGACCAGGCTGGACGGGAAGAATCTGGTGC
AGGAATGGCTGGCGAAGCGCCAGGGTGCCCGGTATGTGTGGAACCGCACTGAGCTCATGCAGGCT
TCCCTGGACCCGTCTGTGACCCATCTCATGGGTCTCTTTGAGCCTGGAGACATGAAATACGAGAT
CCACCGAGACTCCACACTGGACCCCTCCCTGATGGAGATGACAGAGGCTGCCCTGCGCCTGCTGA
GCAGGAACCCCGCGGCTTCTTCCTCTTCGTGGAGGGTGGTCGCATCGACCATGGTCATCATGAA
AGCAGGGCTTACCGGGCACTGACTGAGACGATCATGTTCGACGACGCCATTGAGAGGGCGGGCCA
GCTCACCAGCGAGGAGGACACGCTGAGCCTCGTCACTGCCGACCACTCCCACGTCTTCTCCTTCG
GAGGCTACCCCCTGCGAGGGAGCTCCATCTTCGGCTGGCCCCTGGCAAGGCCCGGGACAGGAAG
GCCTACACGGTCCTCCTATACGGAAACGGTCCAGGCTATGTGCTCAAGGACGGCGCCCGGCCGGA
TGTTACCGAGAGCGAGAGCGGGAGCCCCGAGTATCGGCAGCAGTCAGCAGTGCCCCTGGACGAAG
AGACCCACGCAGGCGAGGACGTGGCGGTGTTCGCGCGCGGCCCGCAGGCGCACCTGGTTCACGGC
GTGCAGGAGCAGACCTTCATAGCGCACGTCATGGCCTTCGCCGCCTGCCTGGAGCCCTACACCGC
CTGCGACCTGGCGCCCCCGCCGGCACCACCGACGCCGCGCACCCGGGTTGAACTAGTCTAGAGA
AAAAACCTCCCACACCTCCCCCTGAACCTGAAACATAAAATGAATGCAATTGTTGTTGTTAACTT
GTTTATTGCAGCTTATAATGGTTACAAATAAAGCAATAGCATCACAAATTTCACAAATAAAGCAT
TTTTTCACTGCATTCTAGTTGTGGTTTGTCCAAACTCATCAATGTATCTTATCATGTCTGGATC
CCCGGGTACCGAGCTCGAATTAATTCCTCTTCCGCTTCCTCGCTCACTGACTCGCTGCGCTCGGT
CGTTCGGCTGCGGCGAGCGGTATCAGCTCACTCAAAGGCGGTAATACGGTTATCCACAGAATCAG
GGGATAACGCAGGAAAGAACATGTGAGCAAAAGGCCAGCAAAGGCCAGGAACCGTAAAAGGCC
GCGTTGCTGGCGTTTTTCCATAGGCTCCGCCCCCCTGACGAGCATCACAAAAATCGACGCTCAAG
TCAGAGGTGGCGAAACCCGACAGGACTATAAAGATACCAGGCGTTTCCCCCTGGAAGCTCCCTCG
TGCGCTCTCCTGTTCCGACCCTGCCGCTTACCGGATACCTGTCCGCCTTTCTCCCTTCGGGAAGC
```

FIG. 2A

GTGGCGCTTTCTCAATGCTCACGCTGTAGGTATCTCAGTTCGGTGTAGGTCGTTCGCTCCAAGCT
GGGCTGTGTGCACGAACCCCCGTTCAGCCCGACCGCTGCGCCTTATCCGGTAACTATCGTCTTG
AGTCCAACCCGGTAAGACACGACTTATCGCCACTGGCAGCAGCCACTGGTAACAGGATTAGCAGA
GCGAGGTATGTAGGCGGTGCTACAGAGTTCTTGAAGTGGTGGCCTAACTACGGCTACACTAGAAG
GACAGTATTTGGTATCTGCGCTCTGCTGAAGCCAGTTACCTTCGGAAAAAGAGTTGGTAGCTCTT
GATCCGGCAAACAAACCACCGCTGGTAGCGGTGGTTTTTTTGTTTGCAAGCAGCAGATTACGCGC
AGAAAAAAAGGATCTCAAGAAGATCCTTTGATCTTTTCTACGGGGTCTGACGCTCAGTGGAACGA
AAACTCACGTTAAGGGATTTTGGTCATGAGATTATCAAAAAGGATCTTCACCTAGATCCTTTTAA
ATTAAAAATGAAGTTTTAAATCAATCTAAAGTATATATGAGTAAACTTGGTCTGACAGTTACCAA
TGCTTAATCAGTGAGGCACCTATCTCAGCGATCTGTCTATTTCGTTCATCCATAGTTGCCTGACT
CCCCGTCGTGTAGATAACTACGATACGGGAGGGCTTACCATCTGGCCCCAGTGCTGCAATGATAC
CGCGAGACCCACGCTCACCGGCTCCAGATTTATCAGCAATAAACCAGCCAGCCGGAAGGGCCGAG
CGCAGAAGTGGTCCTGCAACTTTATCCGCCTCCATCCAGTCTATTAATTGTTGCCGGGAAGCTAG
AGTAAGTAGTTCGCCAGTTAATAGTTTGCGCAACGTTGTTGCCATTGCTACAGGCATCGTGGTGT
CACGCTCGTCGTTTGGTATGGCTTCATTCAGCTCCGGTTCCCAACGATCAAGGCGAGTTACATGA
TCCCCCATGTTGTGCAAAAAAGCGGTTAGCTCCTTCGGTCCTCCGATCGTTGTCAGAAGTAAGTT
GGCCGCAGTGTTATCACTCATGGTTATGGCAGCACTGCATAATTCTCTTACTGTCATGCCATCCG
TAAGATGCTTTTCTGTGACTGGTGAGTACTCAACCAAGTCATTCTGAGAATAGTGTATGCGGCGA
CCGAGTTGCTCTTGCCCGGCGTCAATACGGGATAATACCGCGCCACATAGCAGAACTTTAAAAGT
GCTCATCATTGGAAAACGTTCTTCGGGGCGAAAACTCTCAAGGATCTTACCGCTGTTGAGATCCA
GTTCGATGTAACCCACTCGTGCACCCAACTGATCTTCAGCATCTTTTACTTTCACCAGCGTTTCT
GGGTGAGCAAAAACAGGAAGGCAAAATGCCGCAAAAAAGGGAATAAGGGCGACACGGAAATGTTG
AATACTCATACTCTTCCTTTTTCAATATTATTGAAGCATTTATCAGGGTTATTGTCTCATGAGCG
GATACATATTTGAATGTATTTAGAAAAATAAACAAATAGGGGTTCCGCGCACATTTCCCCGAAAA
GTGCCACCTGC; (SEQ ID NO: 1)

FIG. 2B

MLLLLLLLGLRLQLSLGIIPVEEENPDFWNREAAEALGAAKKLQPAQTAAKNLIIFLGDGMGVST
VTAARILKGQKKDKLGPEIPLAMDRFPYVALSKTYNVDKHVPDSGATATAYLCGVKGNFQTIGLS
AAARFNQCNTTRGNEVISVMNRAKKAGKSVGVVTTTRVQHASPAGTYAHTVNRNWYSDADVPASA
RQEGCQDIATQLISNMDIDVILGGGRKYMFRMGTPDPEYPDDYSQGGTRLDGKNLVQEWLAKRQG
ARYVWNRTELMQASLDPSVTHLMGLFEPGDMKYEIHRDSTLDPSLMEMTEAALRLLSRNPRGFFL
FVEGGRIDHGHHESRAYRALTETIMFDDAIERAGQLTSEEDTLSLVTADHSHVFSFGGYPLRGSS
IFGLAPGKARDRKAYTVLLYGNGPGYVLKDGARPDVTESESGSPEYRQQSAVPLDEETHAGEDVA
VFARGPQAHLVHGVQEQTFIAHVMAFAACLEPYTACDLAPPAGTTDAAHPGRSVVPALLPLLAGT
LLLLETATAP (SEQ ID NO: 2)

FIG. 3

IIPVEEENPDFWNREAAEALGAAKKLQPAQTAAKNLIIFLGDGMGVSTVTAARILKGQKKDKLGP
EIPLAMDRFPYVALSKTYNVDKHVPDSGATATAYLCGVKGNFQTIGLSAAARFNQCNTTRGNEVI
SVMNRAKKAGKSVGVVTTTRVQHASPAGTYAHTVNRNWYSDADVPASARQEGCQDIATQLISNMD
IDVILGGGRKYMFRMGTPDPEYPDDYSQGGTRLDGKNLVQEWLAKRQGARYVWNRTELMQASLDP
SVTHLMGLFEPGDMKYEIHRDSTLDPSLMEMTEAALRLLSRNPRGFFLFVEGGRIDHGHHESRAY
RALTETIMFDDAIERAGQLTSEEDTLSLVTADHSHVFSFGGYPLRGSSIFGLAPGKARDRKAYTV
LLYGNGPGYVLKDGARPDVTESESGSPEYRQQSAVPLDEETHAGEDVAVFARGPQAHLVHGVQEQ
TFIAHVMAFAACLEPYTACDLAPPAGTTDAAHPG (SEQ ID NO: 3)

FIG. 4

```
                                                                                          GGCACGAGGGCGGCTGGGAGCGCGCTGAGCCGCTGCCGCACGGCCGGCCACAGGACCACCTCCCCGGAG  79
       M   W   L   V   T   F   L   L   L   D   S   L   H   K                            15
AATAGGGCCTCTTTATGGC ATG TGG CTG GTA ACT TTC CTC CTG CTG GAC TCT TTA CAC AAA            143

A   R   P   E   D   V   G   T   S   S   L   Y   F   V   N   D   S   L   Q   Q   V      35
GCC CGC CCT GAA GAT GTT GGC ACC AGC AGC CTC TAC TTT GTA AAT GAC TCC TTG CAG CAG GTG    203

T   F   S   S   S   V   G   V   V   P   C   P   A   A   G   S   P   S   A             55
ACC TTT TCC AGC TCC GTG GGG GTG GTG CCC TGC CCG GCC GCG GGC TCC CCC AGC GCG            263

A   L   R   W   Y   L   A   T   G   D   I   Y   D   V   P   H   I   R   H             75
GCC CTT CGA TGG TAC CTG GCC ACA GGG GAC ATC TAC GAC GTG CCG CAC ATC CGG CAC            323

V   H   A   N   G   T   L   Q   Q   L   Y   P   S   P   F   S   A   F   N   S   F      95
GTC CAC GCC AAC GGG ACG CTG CAG CAG CTC TAC CCC TCC CCC TTC TCC GCC TTC AAT AGC TTT    383

I   H   D   N   D   Y   F   C   T   A   E   N   A   A   G   K   I   R   S   P         115
ATC CAC GAC AAT GAC TAC TTC TGC ACC GCG GAG AAC GCT GCC GGC AAG ATC CGG AGC CCC        443

N   I   R   V   K   A   V   F   R   E   P   Y   T   V   R   V   E   D   Q   R         135
AAC ATC CGC GTC AAA GCA GTT TTC AGG GAA CCC TAC ACC GTC CGG GTG GAG GAT CAA AGG        503

S   M   R   G   N   V   F   K   D   T   V   S   L   I   P   S   S   V   Q   E   Y     155
TCA ATG CGT GGC AAC GTC TTC AAG GAC ACA GTC TCC CTC ATC CCC TCT TCA GTG CAG GAA TAT    563

V   S   V   S   W   E   K   G   L   Y   I   S   I   P   E   N   R   F   F             175
GTT AGC GTT TCT TGG GAG AAA GGC CTG TAC ATC TCC ATC CCA GAA AAC AGG TTT TTT            623

I   T   Y   H   G   G   L   Y   I   S   D   V   Q   K   E   D   A   L   S   T         195
ATT ACC TAC CAC GGC GGG CTG TAC ATC TCT GAC GTA CAG AAG GAG GAC GCC CTC TCC ACC        683
```

FIG. 5A

```
Y   R   C   I   T   K   H   K   Y   S   G   E   T   R   Q   S   N   G   A   R    215
TAT CGC TGC ATC ACC AAG CAC AAG TAT AGC GGG GAG ACC CGG CAG AGC AAT GGG GCA CGC  743

L   S   V   T   D   P   A   E   S   I   P   T   I   L   D   G   F   H   S   Q    235
CTC TCT GTG ACA GAC CCT GCT GAG TCG ATC CCC ACC ATC CTG GAT GGC TTC CAC TCC CAG  803

E   V   W   A   G   H   T   V   E   L   P   C   T   A   S   G   Y   P   I   P    255
GAA GTG TGG GCC GGC CAC ACC GTG GAG CTG CCC TGC ACC GCC TCG GGC TAC CCT ATC CCC  863

A   I   R   W   L   K   D   G   R   P   L   P   A   D   S   R   W   T   K   R    275
GCC ATC CGC TGG CTC AAG GAT GGC CGG CCC CTC CCG GCT GAC AGC CGC TGG ACC AAG CGC  923

I   T   G   L   T   I   S   D   R   T   E   D   S   G   T   Y   I   C   E        295
ATC ACA GGG CTG ACC ATC AGC GAC CGG ACC GAG GAC AGC GGC ACC TAC ATT TGT GAG      983

V   T   N   T   F   G   S   A   E   A   T   G   I   L   M   V   I   D   P   L    315
GTC ACC AAC ACC TTC GGT TCG GCA GAG GCC ACA GGC ATC CTC ATG GTC ATT GAT CCC CTT  1043

H   V   T   L   T   P   K   K   L   G   I   K   T   V   I   L   S                335
CAT GTG ACC CTG ACA CCA AAG AAG CTG GGC ATT AAG ACC GTC ATC CTC TCC              1103

C   A   L   T   G   T   S   P   E   F   T   I   R   W   Y   R   N   T   E   L   V  355
TGT GCC CTG ACG GGC ACG TCC CCA GAG TTC ACC ATC CGC TGG TAT CGC AAC ACG GAG CTG GTG 1163
```

FIG. 5B

```
L   P   D   E   A   I   S   I   R   G   L   S   N   E   T   L   L   I   T   S      375
CTG CCT GAC GAG GCC ATC TCC ATC CGT GGG CTC AGC AAC GAG ACG CTG CTC ATC ACC TCG     1223

A   Q   K   S   H   S   G   A   Y   Q   C   F   A   T   R   K   A   Q   T   A      395
GCC CAG AAG AGC CAT TCC GGG GCC TAC CAG TGC TTC GCT ACC CGC AAG GCC CAG ACC GCC     1283

Q   D   F   A   I   I   A   L   E   D   G   T   P   R   I   V   S   F   S          415
CAG GAC TTT GCC ATC ATT GCA CTT GAG GAT GGC ACG CCC CGC ATC GTC TCG TCC TTC AGC     1343

E   K   V   V   N   P   G   E   Q   F   S   L   M   C   A   A   K   G   A   P      435
GAG AAG GTG GTC AAC CCC GGG GAG CAG TTC TCA CTG ATG TGT GCG GCC AAG GGC GCC CCG     1403

P   P   T   V   T   W   A   L   D   Q   D   D   E   P   I   V   R   D   G   S      455
CCC CCC ACG GTC ACC TGG GCC CTC GAC GAT GAG CCC ATC GTG CGG GAT GGC AGC            1463

H   R          465
                                                                    CAC CGC        1493

T   N   Q   Y   T   M   S   D   G   T   (SEQ ID NO: 5)
ACC AAC CAG TAC ACC ATG TCG GAC GGC ACC (SEQ ID NO: 6)
```

FIG. 5C

| 8f26       | ------MWLVTFLLLLDSLHKARPED------------VGTSLYFVNDSLQQVTFSSS |
| D38492     | --MKTPLLVSHLLLISLTSCLGEFTWHRRYGHGVSEEDKGFGPIFEEQPINTIYPEESLE |
| P20241EURO | --MWRQSTILAALLVALLCAGSAESKGNRPPRITK-----QPAPGELLFKVAQQNKESD |
| P32004EURA | ---MVVALRYVWPLLLCSPCLLIQIPEEYEGHHVME-----PPVITEQSPR-RLVVFPTD |
| P35331G-CA | -MMKEKSISASKASLVFFLCQMISALDVPLDSKLLEELS-QPPTITQQSPK-DYIVDPRE |
| Q02246XONI | -MGTATRRKPHLLLVAAVALVSSSAWSSALGSQTT-----FGPVFEDQPLSVLFPEESTE |
| U11031     | ---MLSWKQLILLSFIGCLAGELLL------Q------GPVFVKEPSNSIFPVGSED |
| X65224     | MVLHSHQLTYAGIAFALCLHHLISAIEVPLDSNIQSELP-QPPTITKQSVK-DYIVDPRD |

| 8f26       | VGVVVPCPAAGSPSAALRWYLATGDDIYDVPHIRHVHANG--TLQLYPFSPSAFNSFIHD |
| D38492     | GKVSLNCRARASPFPVYKWRMN-NGDVDLTN-DRYSMV----GGNLVINNPDKQK-D--A |
| P20241EURO | NPFIIECEADGQPEPEYSWIKN-GKKFDWQAYDNRMLRQPG-RGTLVITIPKDED----R |
| P32004EURA | D-ISLKCEASGKPEVQFRWTRD-GVHFKPKEELGVTVYQSPHSGSFTITGNNSNFAQRFQ |
| P35331G-CA | N-IVIQCEAKGKPPPSFSWTRN-GTHFDIDKDAQVTMKPN--SGTLVVNIMNGVKAEAYE |
| Q02246XONI | EQVLLACRARASPPATYRWKMN-GTEMKLEPGSRHQLV----GGNLVIMNPTKAQ-D--A |
| U11031     | KKITLNCEARGNPSPHYRWQLN-GSDIDTSLDHRYKLN----GGNLIVINPNRNW-D--T |
| X65224     | N-IFIECEAKGNPVPTFSWTRN-GKFFNVAKDPKVSMRRR--SGTLVIDFHGGGRPDDYE |

| 8f26       | NDYFCTAENAAGKIRSPNIRVKAVFREPYTVRVEDQRSMR-GNVAVFKCLIPSSVQEYVS |
| D38492     | GIYYCLASNNYGMVRSTEATLSFGYLDPFPPEDRPEVKVKEGKGMVLLCDPPYHFPDD-L |
| P20241EURO | GHYQCFASNEFGTATSNSVYVRKAELNAFKDEAAKTLEAVEGEPFMLKCAAPDGFPS--P |
| P32004EURA | GIYRCFASNKLGTAMSHEIRLMAEGAPKWPKETVKPVEVEEGESVVLPCNPPPSAEP--L |
| P35331G-CA | GVYQCTARNERGAAISNNIVIRPSRSPLWTKEKLEPNHVREGDSLVLNCRPPVGLPP--P |
| Q02246XONI | GVYQCLASNPVGTVVSREAILRFGFLQEFSKEERDPVKAHEGWGVMLPCNPPAHYPG--L |
| U11031     | GSYQCFATNSLGTIVSREAKLQFAYLENFKSRMRSRVSVREGQGVVLLCGPPPHSGE--L |
| X65224     | GEYQCFARNDYGTALSSKIHLQVSRSPLWPKEKVDIEVDEGAPLSLQCNPPPGLPP--P |

FIG. 6A

```
8f26        VVSWEKDTVSIIPE------NR--FFITYHGGLYIISDVQKED--ALSTYRCITKHKYSGET
D38492      SYRWLLNEFPVFITM---DKRRFVSQ-TNGNLYIANVESSD---RGNYSCFVSS--PSIT
P20241EURO  TVNWMIQESIDGSIKSINNSR--MTLDPEGNLWFSNVTREDASSDFYYACSATSVFRSEY
P32004EURA  RIYWMNSKILHIKQ------DER--VTMGQNGNLYFANVLTSDN--HSDYICHAHFPGTRTI
P35331G-CA  IIFWMDNAFQRLPQ------SER--VSQGLNGDLYFSNVQPEDT--RVDYICYARFNHTQTI
Q02246XONI  SYRWLLNEFPNFIPT---DGRHFVSQ-TTGNLYIARTNASD---LGNYSCLATSHMDFST
U11031      SYAWVFNEYPSFVEE---DSRRFVSQ-ETGHLYIAKVEPSD---VGNYTCVVTS--TVTN
X65224      VIFWMSSSMEPIHQ-----DKR---VSQGQNGDLYFSNVMLQDA--QTDYSCNARFHFTHTI
                              *                         *

8f26        RQSNGARLSVTDPAES----------------------------IPTILDGFHSQEV----WAGHTVEL
D38492      KSVFSKFIPLIPIPERTT-----------------KPYPADIVVQFKDIY--TMMGQNVTL
P20241EURO  KIGNKVLLDVKQMGVSASQ---------------NKHPPVRQYVSRRQS-LALRGKRMEL
P32004EURA  IQKEPIDLRVKATNSMID---------------RKPRLLFPTNSSHLVALQGQPLVL
P35331G-CA  QQKQPISVKVFSTKP------------------VTERPPVLLTPMGSTSNKVELRGNVLLL
Q02246XONI  KSVFSKFAQLNLAAEDTR---------------LFAPSIKARFPAETY--ALVGQQVTL
U11031      ARVLGSPTPLVLRSDGVMG--------------EYEPKIELQFPETLP--AAKGSTVKL
X65224      QQKNPYTLKVTKKPHNETSLRNHTDMYSARGVTETTPSFMYPYGTSSSQMVLRGVDLLL
                   *                                   *             *

8f26        PCTASGYPIPAIRWLKDGRP--LPADSRWTKRITGLTISDLRTEDSGTYICEVTNTFGSA
D38492      ECFALGNPVPDIRWRKVLEP--MPTTAEISTSGAVLKIFNIQLEDEGLYECEAENIRGKD
P20241EURO  FCIYGGTPLPQTVWSKDGQRIQWSDRITQGHYGKSLVIRQTNFDDAGTYTCDVSNGVGNA
P32004EURA  ECIAEGFPTPTIKWLRPSGPM--PADRVTYQNHNKTLQLLKVGEEDDGEYRCLAENSLGSA
P35331G-CA  ECIAAGLPTPVIRWIKEGGEL--PANRTFFENFKKTLKIIDVSEADSGNYKCTARNTLGST
Q02246XONI  ECFAFGNPVPRIKWRKVDG-----SLSPQWTTAEPTLQIPSVSFEDEGTYECEAENSKGRD
U11031      ECFALGNPVPQINWRRSDGMP--FPTKIKLRKFNGVLEIPNFQQEDTGSYECIAENSRGKN
X65224      ECIASGVPAPDIMWYKKGGEL-PAGKTKLENFNKALRISNVSEEDSGEYFCLASNKMGSI
              *   *        *                *    *    *     *     *

FIG. 6B
```

```
8f26       E-ATGILMVIDPLHVTLTPKKLKTGIGSTVILSCALTGSPEFTIRWYRNT-------------
D38492     K-HQARIYVQAFPEWVEHINDTEVDIGSDLYWPCVATGKPIPTIRWLKNG-------------
P20241EURO QSFSIILNVNSVPYFTKEPEIATAAEDEEVVFECRAAGVPEPKISWIHNGKPIEQSTPNP
P32004EURA R-HAYYVTVEAAPYWLHKPQSHLYGPGETARLDCQVQGRPQPEVTWRINGIPVEELAKDQ
P35331G-CA H-HVISVTVKAAPYWITAPRNLVLSPGEDGTLICRANGNPKPSISWLTNGVPIAIAPEDP
Q02246XONI T-VQGRIIVQAQPEWLKVISDTEADIGSNLRWGCAAAGKPRPTVRWLRNGEPLASQNR--
U11031     V-ARGRLTYYAKPYWVQLLKDVETAVEDSLYWECRASGKPKPSYRWLKNGDALVLEER---
X65224     R-HTISVRVKAAPYWLDEPQNLILAPGEDGRLVCRANGNPKPSIQWLVNGEPIEGSPPNP
                                               *        *       *

8f26       ----E---------------------LVLPDEAISIRGLSN-------------------
D38492     -YAYHKGELRLYDVTFENAGMYQCIAENAYGTIYANAELKILALAPTFEMNPMKKILAA
P20241EURO RRTVTDNTIRIINLVKGDTGNYGCNATNSLGYVYKDVYLNVQAEPP--TISEAPAAVSTV
P32004EURA KYRIQRGALILSNVQPSDTMVTQCEARNRHGLLLANAYIYVVQLPA-KILTADNQTYMAV
P35331G-CA SRKVDGDTIIFSAVQERSSAVYQCNASNEYGYLLANAFVNVLAEPP-RILTPANKLYQVI
Q02246XONI -VEVLAGDLRFSKLSLEDSGMYQCVAENKHGTIYASAELAVQALAPDFRLNPVRRLIPAA
U11031     -IQIENGALTIANLNVSDSGMFQCIAENKHGLIYSSAELKVLASAPDFSRNPMKKMIQVQ
X65224     SREVAGDTIVFRDTQIGSSAVYQCNASNEHGYLLANAFVSVLDVPP-RILAPRNQLIKVI
                          *                               *

8f26       ----------------------------ETLLITSAQKSHSGAYQCFA
D38492     KGGRVIIECKPKAAPKPKFSWSKGTEWLVNSSRILIWED-GSLEINNITRNDGGIYTCFA
P20241EURO DGRNVTIKCRVNGSPKPLVKWLRASNWLT--GGRYNVQANGDLEIQDVTFSDAGKYTCYA
P32004EURA QGSTAYLLCKAFGAPVPSVQWLDEDGTTVLQDERFFPYANGTLGIRDLQANDTGRYFCLA
P35331G-CA ADSPALIDCAYFGSPKPEIEWFRGVKGSILRGNEYVFHDNGTLEIPVAQKDSTGTYTCVA
Q02246XONI RGGEILIPCQPRAAPKAVVLWSKGTEILVNSSRVTVTPD-GTLIIRNISRSDEGKYTCFA
U11031     VGSLVILDCKPSASPRALSFWKKGDTVVREQARISLLND-GGLKIMNVTKADAGIYTCIA
X65224     QYNRTRLDCPFFGSPIPTLRWFKNGQGNMLDGGNYKAHENGSLEMSMARKEDQGIYTCVA
                                              *  *     *

FIG. 6C
```

```
8f26         TRKAQTAQDFAIIALEDGTPRIVSSFSEKVVNPGEQFSLMCAAKGAP--PPTVTWALDDE
D38492       ENNRGKANSTGTLVITNPT-RIILAPINADITVGENATMQCAASFDPSLDLTFVWSFNGY
P20241EURO   QNKFGEIQADGSLVVKEHT-RITQEPQNYEVAAGQSATFRCNEAHDDTLEIEIDWWKDGQ
P32004EURA   ANDQNNVTIMANLKVKDAT-QITQGPRSTIEKKGSRVTFTCQASFDPSLQPSITWRGDGR
P35331G-CA   RNKLGKTQNEVQLEVKDPT-MIIKQPQYKVIQRSAQASFECVIKHDPTLIPTVIWLKD--
Q02246XONI   ENFMGKANSTGILSVRDAT-KITLAPSSADINLGDNLTLQCHASHDPTMDLTFTWTLDDF
U11031       ENQFGKANGTTQLVVTEPT-RIILAPSNMDVAVGESIILPCQVQHDPLLDIMFAWYFNGT
X65224       TNILGKVEAQVRLEVKDPT-RIVRGPEDQVVKRGSMPRLHCRVKHDPTLKLTVTWLKD--
                       *                  .                       *

8f26         PIVRDGSHRTNQYTMS--------------------------------             (SEQ ID NO: 7)
D38492       VIDFNKEITNIHYQRNFMLDANGELLIRNAQLKHAGRYTCTAQTIVDNSSASADLVVRGP (SEQ ID NO: 8)
P20241EURO   SIDFEAQPR-----FVKTNDN--SLTIAKTMELDSGEYTCVARTRLDEATARANLIVQDV (SEQ ID NO: 9)
P32004EURA   --DLQELGD---SDKYFIEDG--RLVIHSLDYSDQGNYSCVASTELDVVESRAQLLVVGS (SEQ ID NO:10)
P35331G-CA   --NNELPDD----ERFLVGKD--NLTIMNVTDKDDGTYTCIVNTTLDSVSASAVLTVVAA (SEQ ID NO:11)
Q02246XONI   PIDFDKPGG--HYRRTNVKETIGDLTILNAQLRHGGKYTCMAQTVVDSASKEATVLVRGP (SEQ ID NO:12)
U11031       LTDFKKDGS--HFEKVGGSSS-GDLMIRNIQLKHSGKYVCMVQTGVDSVSSAAELIVRGS (SEQ ID NO:13)
X65224       --DAPLYIG----NRMKKEDD--GLTIYGVAEKDQGDYTCVASTELDKDSAKAYLTVLAI (SEQ ID NO:14)
```

FIG. 6D

SECRETED NEURAL ADHESION PROTEINS

RELATED APPLICATION INFORMATION

This application is a divisional of U.S. application Ser. No. 09/707,802, filed Nov. 9, 2000, which is a continuation of U.S. application Ser. No. 09/283,503, filed Apr. 1, 1999, now abandoned, which is a divisional of U.S. application Ser. No. 08/752,307, filed Nov. 19, 1996, now U.S. Pat. No. 5,952,171, issued Sep. 14, 1999. The contents of these patents and patent applications are incorporated herein by the references.

BACKGROUND OF THE INVENTION

The invention relates to methods for identifying genes encoding novel proteins.

There is considerable medical interest in secreted and membrane-associated mammalian proteins. Many such proteins, for example, cytokines, are important for inducing the growth or differentiation of cells with which they interact or for triggering one or more specific cellular responses.

An important goal in the design and development of new therapies is the identification and characterization of secreted proteins and the genes which encode them. Traditionally, this goal has been pursued by identifying a particular response of a particular cell type and attempting to isolate and purify a secreted protein capable of eliciting the response. This approach is limited by a number of factors. First, certain secreted proteins will not be identified because the responses they evoke may not be recognizable or measurable. Second, because in vitro assays must be used to isolate and purify secreted proteins, somewhat artificial systems must be used. This raises the possibility that certain important secreted proteins will not be identified unless the features of the in vitro system (e.g., cell line, culture medium, or growth conditions) accurately reflect the in vivo milieu. Third, the complexity of the effects of secreted proteins on the cells with which they interact vastly complicates the task of isolating important secreted proteins. Any given cell can be simultaneously subject to the effects of two or more secreted proteins. Because any two secreted proteins will not have the same effect on a given cell and because the effect of a first secreted protein on a given cell can alter the effect of a second secreted protein on the same cell, it can be difficult to isolate the secreted protein or proteins responsible for a given physiological response. In addition, certain secreted and membrane-associated proteins may be expressed at levels that are too low to detect by biological assay or protein purification.

In another approach, genes encoding secreted proteins have been isolated using DNA probes or PCR oligonucleotides which recognize sequence motifs present in genes encoding known secreted protein. In addition, homology-directed searching of Expressed Sequence Tag (EST) sequences derived by high-throughput sequencing of specific cDNA libraries has been used to identify genes encoding secreted proteins. These approaches depend for their success on a high degree of similarity between the DNA sequences used as probes and the unknown genes or EST sequences.

More recently, methods have been developed that permit the identification of cDNAs encoding a signal sequence capable of directing the secretion of a particular protein from certain cell types. Both Honjo, U.S. Pat. No. 5,525,486, and Jacobs, U.S. Pat. No. 5,536,637, describe such methods. These methods are said to be capable of identifying secreted proteins.

The demonstrated clinical utility of several secreted proteins in the treatment of human disease, for example, erythropoietin, granulocyte-macrophage colony stimulating factor (GM-CSF), human growth hormone, and various interleukins, has generated considerable interest in the identification of novel secreted proteins. The method of the invention can be employed as a tool in the discovery of such novel proteins.

SUMMARY OF THE INVENTION

The invention features a method for isolating cDNAs and identifying encode secreted or membrane-associated (e.g. transmembrane) mammalian proteins. The method of the invention relies upon the observation that the majority of secreted and membrane-associated proteins possess at their amino termini a stretch of hydrophobic amino acid residues referred to as the "signal sequence." The signal sequence directs secreted and membrane-associated proteins to a sub-cellular membrane compartment termed the endoplasmic reticulum, from which these proteins are dispatched for secretion or presentation on the cell surface.

The invention describes a method in which cDNAs that encode signal sequences for secreted or membrane-associated proteins are isolated by virtue of their abilities to direct the export of the reporter protein, alkaline phosphatase (AP), from mammalian cells. The present method has major advantages over other signal peptide trapping approaches. The present method is highly sensitive. This facilitates the isolation of signal peptide associated proteins that may be difficult to isolate with other techniques. Moreover, the present method is amenable to throughput screening techniques and automation. Combined with a novel method for cDNA library construction in which directional random primed cDNA libraries are prepared, the invention comprises a powerful and approach to the large scale isolation of novel secreted proteins.

The invention features a method for identifying a cDNA nucleic acid encoding a mammalian protein having a signal sequence, which method includes the following steps:

a) providing library of mammalian cDNA;

b) ligating the library of mammalian cDNA to DNA encoding alkaline phosphatase lacking both a signal sequence and a membrane anchor sequence to form ligated DNA;

c) transforming bacterial cells with the ligated DNA to create a bacterial cell clone library;

d) isolating DNA comprising the mammalian cDNA from at least one clone in the bacterial cell clone library;

e) separately transfecting DNA isolated from clones in step (d) into mammalian cells which do not express alkaline phosphatase to create a mammalian cell clone library wherein each clone in the mammalian cell clone library corresponds to a clone in the bacterial cell clone library;

f) identifying a clone in the mammalian cell clone library which express alkaline phosphatase;

g) identifying the clone in the bacterial cell clone library corresponding to the clone in the mammalian cell clone library identified in step (f); and h) isolating and sequencing a portion of the mammalian cDNA present in the bacterial cell library clone identified in step (g) to identify a mammalian cDNA encoding a mammalian protein having a signal sequence.

A cDNA library is a collection of nucleic acid molecueles that are a cDNA copy of a sample of mRNA.

In another aspect, the invention features ptrAP3 expression vector.

In another aspect, the invention features a substantially pure preparation of ethb0018f2 protein. Preferably, the ethb0018f2 protein includes an amino acid sequence substantially identical to the amino acid sequence shown in FIG. 5 (SEQ ID NO: 5); is derived from a mammal, for example, a human.

The invention also features purified DNA (for example, cDNA) which includes a sequence encoding a ethb0018f2 protein, preferably encoding a human ethb0018f2 protein (for example, the ethb0018f2 protein of FIG. 5; SEQ ID NO:5); a vector and a cell which includes a purified DNA of the invention; and a method of producing a recombinant ethb0018f2 protein involving providing a cell transformed with DNA encoding ethb0018f2 protein positioned for expression in the cell, culturing the transformed cell under conditions for expressing the DNA, and isolating the recombinant ethb0018f2 protein. The invention further features recombinant ethb0018f2 protein produced by such expression of a purified DNA of the invention.

By "ethb0018f2 protein" is meant a polypeptide which has a biological activity possessed by naturally-occuring ethb0018f2 protein. Preferably, such a polypeptide has an amino acid sequence which is at least 85%, preferably 90%, and most preferably 95% or even 99% identical to the amino acid sequence of the ethb0018f2 protein of FIG. 5 (SEQ ID NO: 5).

By "substantially identical" is meant a polypeptide or nucleic acid having a sequence that is at least 85%, preferably 90%, and more preferably 95% or more identical to the sequence of the reference amino acid or nucleic acid sequence. For polypeptides, the length of the reference polypeptide sequence will generally be at least 16 amino acids, preferably at least 20 amino acids, more preferably at least 25 amino acids, and most preferably 35 amino acids. For nucleic acids, the length of the reference nucleic acid sequence will generally be at least 50 nucleotides, preferably at least 60 nucleotides, more preferably at least 75 nucleotides, and most preferably 110 nucleotides.

Sequence identity can be measured using sequence analysis software (e.g., Sequence Analysis Software Package of the Genetics Computer Group, University of Wisconsin Biotechnology Center, 1710 University Avenue, Madison, Wis. 53705).

In the case of polypeptide sequences which are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Where a particular polypeptide is the to have a specific percent identity to a reference polypeptide of a defined length, the percent identity is relative to the reference peptide. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide which is 50% identical to the reference polypeptide over its entire length. Of course, many other polypeptides will meet the same criteria.

By "protein" and "polypeptide" is meant any chain of amino acids, regardless of length or post-translational modification (e.g., glycosylation of phosphorylation).

By "substantially pure" is meant a preparation which is at least 60% by weight (dry weight) the compound of interest, i.e., a ethb0018f2 protein. Preferably the preparation is at least 75%, more preferably at least 90%, and most preferably at least 99%, by weight the compound of interest. Purity can be measured by any appropriate method, e.g., column chromatography, polyacrylamide gel electrophoresis, or HPLC analysis.

By "purified DNA" is meant DNA that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA which is part of a hybrid gene encoding additional polypeptide sequence.

By "substantially identical" is meant an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein (assayed, e.g., as described herein). Preferably, such a sequence is at least 85%, more preferably 90%, and most preferably 95% identical at the amino acid level to the sequence of FIG. 5 (SEQ ID NO: 5). For nucleic acids, the length of comparison sequences will generally be at least 50 nucleotides, preferably at least 60 nucleotides, more preferably at least 75 nucleotides, and most preferably 110 nucleotides. A "substantially identical" nucleic acid sequence codes for a substantially identical amino acid sequence as defined above.

By "transformed cell" is meant a cell into which (or into an ancestor of which) has been introduced, by means of recombinant DNA techniques, a DNA molecule encoding (as used herein) ethb0018f2 protein.

By "positioned for expression" is meant that the DNA molecule is positioned adjacent to a DNA sequence which directs transcription and translation of the sequence (i.e., facilitates the production of ethb0018f2 protein).

By "purified antibody" is meant antibody which is at least 60%, by weight, free from the proteins and naturally-occurring organic molecules with which it is naturally associated. Preferably, the preparation is at least 75%, more preferably at least 90%, and most preferably at least 99%, by weight, antibody.

By "specifically binds" is meant an antibody which recognizes and binds ethb0018f2 protein but which does not substantially recognize and bind other molecules in a sample, e.g., a biological sample, which naturally includes ethb0018f2 protein.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIGS. 2A–2B is a representation of the DNA sequence of the ptrAP3 vector (SEQ ID NO:1). The bold, underlined portion is the small fragment removed prior to cDNA insertion sequence. The italic, underlined portion is the alkaline phosphatase sequence.

FIG. 3 is a representation of the amino acid sequence of human placental alkaline phosphatase (Accession No. P05187). The underlined portion is the signal sequence. The bold, underlined portion is the membrane anchor sequence.

FIG. 4 is a representation of the amino acid sequence of the alkaline phosphatase encoded by ptrAP3.

FIGS. 5A–5C is a representation of the cDNA and amino acid sequence of a portion of a novel secreted protein identified using the method described in Example 1.

FIGS. 6A–6D is a representation of an alignment of the amino acid sequence of clone ethb0018f2 (referred to here as 8f2) and proteins containing conserved IgG domains. The proteins are D38492 (neural adhesion molecule f3); P20241EURO (Drosophila Neuroglian); P32004EURA (human neural adhesion molecule L1); P35331G-CA (chick neural adhesion molecule related protein); Q02246XONI (human Axonin 1); U11031 (rat neural adhesion molecule BIG1); and X65224 (chicken Neurofascin) are depicted. In these figures, conserved motifs within the IgG domain are highlighted in bold.

DETAILED DESCRIPTION

Figure 1:
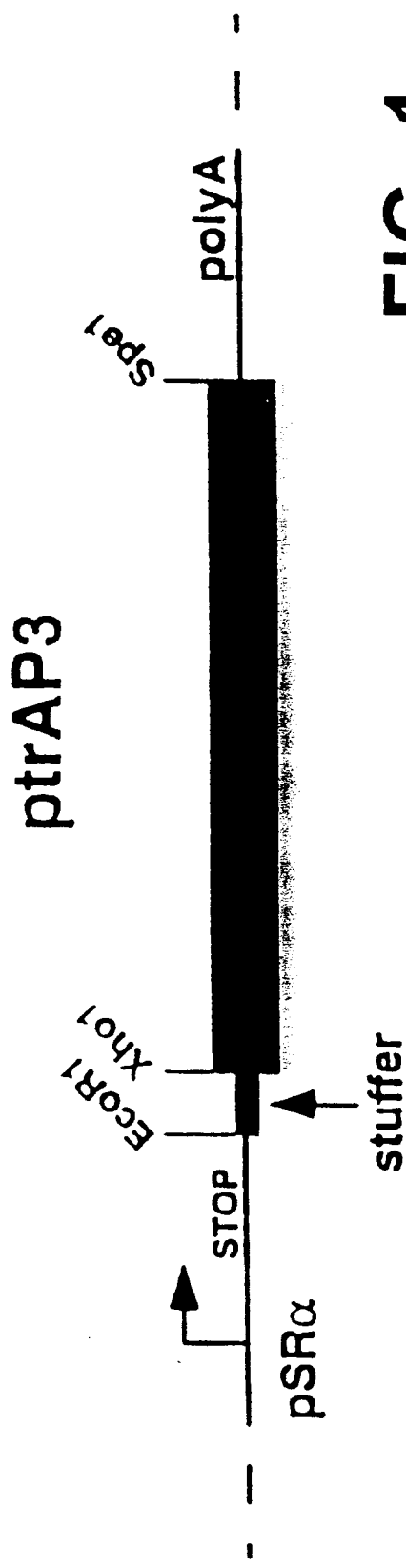
FIG. 1 is a schematic drawing of a portion of the ptrAP3 vector.

In general terms, the method of the invention entails the following steps:

1. Preparation of a randomly primed cDNA library using cDNA prepared from mRNA extracted from mammalian cells or tissue. The cDNA is inserted into a mammalian expression vector adjacent to a cDNA encoding placental alkaline phosphatase which lacks a secretory signal.

2. Amplification of the cDNA library in bacteria.

3. Isolation of the cDNA library.

4. Transfection of the resulting cDNA library into mammalian cells.

5. Assay of supernatants from the transfected mammalian cells for alkaline phosphatase activity.

6. Isolation and sequencing of plasmid DNA clones registering a positive score in the alkaline phosphatase assay.

7. Isolation of full length cDNA clones of novel proteins having a signal sequence.

The mammalian cDNA used to create the cDNA library can be prepared using any known method. Generally, the cDNA is produced from mRNA. The mRNA can be isolated from any desired tissue or cell type. For example, peripheral blood cells, primary cells, tumor cells, or other cells may be used as a source of mRNA.

The expression vector harboring the modified alkaline phosphatase gene can be any vector suitable for expression of proteins in mammalian cells.

The mammalian cells used in the transfection step can be any suitable mammalian cells, e.g., CHO cells, mouse L cells, Hela cells, VERO cells, mouse 3T3 cells, and 293 cells.

Described below is a specific example of the method of the invention. Also described below are two genes, one known and one novel, identified using this method.

EXAMPLE I

Step 1

Generation of Mammalian Signal Peptide Trap cDNA Libraries

Vector

A cDNA library was prepared using ptrAP3, a mammalian expression vector containing a cDNA encoding human placental alkaline phosphatase (AP) lacking a signal sequence (FIG. 1 and FIG. 2, SEQ ID NO:1). When ptrAP3 is transfected into a mammalian cell line, such as COS7 cells, AP protein is neither expressed nor secreted since the AP cDNA of ptraAP3 does not encode a translation initiating methionine, a signal peptide, or a membrane anchor sequence. FIG. 3 (SEQ ID NO:2) provides the amino acid sequence of naturally occurring AP. FIG. 4 (SEQ ID NO:3) provides the amino acid sequence of the form of AP encoded by ptrAP3. However, insertion of a cDNA encoding a signal peptide sequence into ptrAP3 such that the signal sequence within the cDNA is fused to and in frame with AP, facilities both the expression and secretion of AP protein upon transfection of the DNA into COS7 cells or other mammalian cells. The presence of AP activity in the supernatants of transfected COS7 cells therefore indicates the presence of a signal sequence in the cDNA of interest.

cDNA Synthesis and Ligation cDNA for ligation to the ptrAP3 vector was prepared from messenger RNA isolated from human fetal brain tissue (Clontech, Palo Alto, Calif.: Catalog #6525-1) by a modification of a commercially available "ZAP cDNA synthesis kit" (Stratagene; La Jolla, Calif.: Catalog #200401). Synthesis of cDNA involved the following steps.

(a) Single stranded cDNA was synthesized from 5 μg of human fetal brain messenger RNA using a random hexamer primer incorporating a XhoI restriction site (underlined); 5'-CTGACTCGAGNNNNNN-3' (SEQ ID NO:4). This represented a deviation from the Stratagene protocol and resulted in a population of randomly primed cDNA molecules. Random priming was employed rather than the oligo d(T) priming method suggested by Stratagene in order to generate short cDNA fragments, some of which would be expected to be mRNAs that encode signal sequences.

(b) The single stranded cDNA generated in step (a) was rendered double stranded, and DNA linkers containing a free EcoR1 overhang were ligated to both ends of the double stranded cDNAs using reagents and protocols from the Stratagene ZAP cDNA synthesis kit according to the manufacturer's instructions.

(c) The linker-adapted double-stranded cDNA generated in step (b) was digested with XhoI to generate a free XhoI overhang at the 3' end of the cDNAs using reagents from the Stratagene ZAP cDNA synthesis kit according to the manufacturers instructions.

(d) Linker-adapted double-stranded cDNAs were size selected by gel filtration through SEPHACRYL™ S-500 cDNA Size Fractionation Columns (Gibco BRL; Bethesda, Md.: Catalog #18092-015) according to the manufacturers instructions.

(e) Size selected, double-stranded cDNAs containing a free EcoR1 overhang at the 5' end and a free XhoI overhang at the 3' end were ligated to the ptrAP3 backbone which had been digested with EcoR1 and XhoI and purified from the small, released fragment by agarose gel electrophoresis.

(f) Ligated plasmid DNAs were transformed into *E. coli* strain DH10b by electroporation.

This process resulted in a library of cDNA clones composed of several million random primed cDNAs (some of which will encode signal sequences) prepared from human fetal brain messenger RNA, fused to the AP reporter cDNA, in the mammalian expression vector ptrAP3.

Step 2

Plating and Automated Picking of Bacterial Colonies

Next, the transformed bacterial cells were plated, and individual clones were identified. A sample of transformed *E. coli* containing the random primed human fetal brain cDNA library described in Step 1 was plated for growth as individual colonies, using standard procedures. Each *E. coli* colony contained an individual cDNA clone fused to the AP reporter in the ptrAP3 expression vector. Approximately 20,000 such *E. coli* colonies were plated, representing approximately 0.5% of the total cDNA library.

Next, *E. coli* colonies were picked from the plates and inoculated into deep well 96 well plates containing 1 ml of growth medium prepared by standard procedures. Colonies were picked from the plates and *E. coli* cultures were grown overnight by standard procedures. Each plate was identified by number. Within each plate, each well contained an individual cDNA clone in the ptrAP vector identified by well position.

Finally, plasmid DNA was extracted from the overnight *E. coli* cultures using a semi-automated 96-well plasmid DNA miniprep procedure, employing standard procedures for bacterial lysis, genomic DNA precipitation and plasmid DNA purification.

The plasmid DNA extraction was performed as follows:

(a) *E. coli* were centrifuged for 20 minutes using a Beckman Centrifuge at 3200 rpm.

(b) Supernatant was discarded and *E. coli* pellets were resuspended in 130 µl WP1 (50 mM TRIS (pH 7.5), 10 mM EDTA, 100 µg/ml RNase A) resuspension solution using a TITERTECK MULTIDROP™ apparatus.

(c) *E. coli* pellets were resuspended by vortexing.

(d) 130 µl WP2 (0.2 M NaOH, 0.5% SDS) lysing solution was added to each well, and the samples were mixed by vortexing for 5 seconds.

(e) 130 µl WP3 (125 mM potassium acetate, pH 4.8) neutralizing solution was added to each well, and the samples were mixed by vortexing for 5 seconds.

(f) Samples were placed on ice for 15 minutes, mixed by vortexing for 5 seconds, and recentrifuged for 10 minutes at 3200 rpm in a Beckman Centrifuge.

(g) Supernatant (crude DNA extract) was transferred from each well of each 96 well plate into a 96 well filter plate (Polyfiltronics) using a TOMTEC/Quadra 96™ transfer apparatus.

(h) 480 µl of Wizard™ Midiprep DNA Purification Resin (Promega) was added to each well of each plate containing crude DNA extract using a Titertek Multidrop apparatus and the samples were left for 5 minutes.

(i) Each 96 well filter plate was placed on a vacuum housing (Polyfiltronics) and the liquid in each well was removed by suction generated by vacuum created with a Lab Port Vacuum pump.

(j) The Wizard Midiprep DNA Purification Resin in each well (to which plasmid DNA was bound) was washed four times with 600 µl of Wizard Wash™.

(k) Plates were centrifuged for 5 minutes to remove excessive moisture from the Wizard Midiprep DNA Purification Resin.

(l) Purified plasmid DNAs were eluted from the Wizard Midiprep DNA Purification Resin into collection plates by addition of 50 µl deionized water to each well using a Multidrop 8 Channel Pipette, incubation at room temperature for 15 minutes, and centrifugation for 5 minutes (3200 rpm, Beckman centrifuge).

This process resulted in preparation of plasmid DNA contained in 96 well plates with each well containing an individual cDNA clone ligated in the ptrAP expression vector. Individual clones were identified by plate number and well position.

Step 4

Transfection of DNAs into COS7 Cells

To determine which of the cDNA clones contained within the cDNA library encoded functional signal peptides, individual plasmid DNA preparations were transfected into COS7 cells as follows.

For each 96 well plate of DNA preparations, one 96 well tissue culture plate containing approximately 10,000 COS7 cells per well was prepared using standard procedures.

Immediately prior to DNA transfection, the COS7 cell culture medium in each well of each 96 well plate was replaced with 80 µl of OptiMEM (Gibco-BRL; catalog #31985-021) containing 1 µl of lipofectamine (Gibco-BRL) and 2 µl (approximately 100–200 ng) of DNA prepared as described above. Thus, each well of each 96 well plate containing COS7 cells received DNA representing one individual cDNA clone from the cDNA library in ptrAP3. The COS7 cells were incubated with the Opti-MEM/Lipofectamine/DNA mixture overnight to allow transfection of cells with the plasmid DNAs.

After overnight incubation, the transfection medium was removed from the cells and replaced with 80 µl fresh medium composed of Opti-MEM+1% fetal calf serum. Cells were incubated overnight.

Step 5

Alkaline Phosphatase Assay

The secreted alkaline phosphatase activity of the transfected COS7 cells was measured as follows. Samples (10 µl) of supernatants from the transfected COS7 cells were transferred from each well of each 96 well plate into one well of a Microfluor scintillation plate (Dynatech:Location Catalog #011-010-7805). AP activity in the supernatants was determined using the Phospha-Light Kit (Tropix Inc.; catalog #BP300). AP assays were performed according to the manufacturer's instruction using a Wallace Micro-Beta scintillation counter.

Step 6

Sequencing and Analysis of Positive Clones

The individual plasmid DNAs scoring positive in the COS7 cell AP secretion assay were analyzed further by DNA sequencing using standard procedures. The resulting DNA sequence information was used to perform BLAST sequence similarity searches of nucleotide protein databases to ascertain whether the clone in question encodes either 1) a known secreted or membrane-associated protein possessing a signal sequence, or 2) a putative novel, secreted or membrane-associated protein possessing a putative novel signal sequence.

Identification of the Protein Tyrosine Phosphatase Sigma (PTPσ) Signal Sequence by Mammalian Signal Peptide trAP Employing the method described in Example 1, a cDNA clone designated ethb005c07 was found to score positive in the COS7 cell transfection AP assay. BLAST similarity searching with the DNA sequence from this clone identified ethb005c07 as a cDNA encoding the signal sequence of protein tyrosine phosphatase sigma (PTPσ), a previously described protein that is well established in the scientific literature to be a transmembrane protein (Pulido et al., *Proc. Nat'l Acad. Sci. USA* 92:11686, 1995).

Identification of a Novel Immunoglobulin Domain Containing Protein by Mammalian Signal Peptide trAP Employing the method described in Example 1, a cDNA clone designated ethb0018f2 was found to score positive in the COS7 cell transfection AP assay. DNA sequencing revealed that ethb0018f2 harbors a 1455 base pair cDNA having a single open reading frame commencing at nucleotide 55 and continuing to nucleotide 1455. Thus, the ethb0018f2 cDNA encodes a 465 amino acid open reading frame (FIG. 5, SEQ ID NO:5) fused to the AP reporter. Inspection of the ethb0018f2 protein sequence revealed the presence of a putative signal sequence between amino acids 1 to 20, predicted by the signal peptide prediction algorithm, signal P (Von Heijne, Nucleic Acids. Reg. 14:4683–90, 1986). Thus, ethb0018f2 encodes a partial clone of a novel putative secreted/membrane protein. BLAST similarity searching of nucleic acid and protein databases with the ethb0018f2 DNA sequence from this clone revealed similarity to a family of proteins known to contain a protein motif referred to as an Immunoglobulin of IgG domain.

Further visual inspection of the ethb0018f2 protein sequence resulted in the identification of 5 consecutive IgG repeats, defined by a conserved spacing of cysteine, tryptophan, tyrosine, and cysteine residues (FIG. 5).

FIG. 6 is a depiction of a protein sequence alignment between clone ethb0018f2 (referred to as 8f2) and seven related proteins known to contain IgG domains that are also known to be expressed in the brain. These proteins are rat neural adhesion molecule f3 (D38492), Drosophila Neuroglian (P20241), human neural adhesion molecule L1 (P32004), chick neural adhesion molecule related (P35331), human Axonin 1 (Q02246), rat neural adhesion molecule BIG1 (U11031) and chicken Neurofascin (X65224). Given this sequence similarity, it is likely that clone ethb0018f2 represents a partial cDNA cone representing a novel protein, expressed in the brain, which contains multiple, consecutive IgG domains. Specifically, since the closest relatiaves of clone ethb0018f2 are believed to function as neural adhesion molecules, it is likely that clone ethb0018f2 represents a partial cDNA clone of a novel neural adhesion molecule.

Other Embodiments

It is to be understood that while the invention has been described in conjunction with the detailed description thereof, that the foregoing description is intended to illustrate and not limit the scope of the invention, which is defined by the scope of the appended claims.

What is claimed is:

1. An isolated polypeptide encoded by the nucleic acid of SEQ ID NO:6.

2. An isolated polypeptide comprising the amino acid sequence of SEQ ID NO:5.

3. An isolated polypeptide consisting of the amino acid sequence of SEQ ID NO:5.

4. The polypeptide as in any one of claims 1 to 3 further comprising a heterologous polpeptide.

5. An isolated polypeptide comprising at least 20 contiguous amino acid residues of SEQ ID NO:5.

6. The polypeptide of claim 5 wherein the polypeptide comprises at least 25 contiguous amino acid residues of SEQ ID NO:5.

7. The polypeptide of claim 5 wherein the polypeptide comprises at least 35 contiguous amino acid residues of SEQ ID NO:5.

8. The polypeptide of claim 4 wherein the heterologous polypeptide comprises an immunoglobulin (Ig) domain.

* * * * *

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
      (A) LENGTH: 4951 base pairs
      (B) TYPE: nucleic acid
      (C) STRANDEDNESS: single
      (D) TOPOLOGY: linear (xi) SEQUENCE DESCRIPTION: SEQ ID NO: 1:

```
AAGCTTGGCT GTGGAATGTG TGTCAGTTAG GGTGTGGAAA GTCCCCAGGC T CCCCAGCAG      60

GCAGAAGTAT GCAAAGCATG CATCTCAATT AGTCAGCAAC CAGGTGTGGA A AGTCCCCAG     120

GCTCCCCAGC AGGCAGAAGT ATGCAAAGCA TGCATCTCAA TTAGTCAGCA A CCATAGTCC     180

CGCCCCTAAC TCCGCCCATC CCGCCCCTAA CTCCGCCCAG TTCCGCCCAT T CTCCGCCCC     240

ATGGCTGACT AATTTTTTTT ATTTATGCAG AGGCCGAGGC CGCCTCGGCC T CTGAGCTAT     300

TCCAGAAGTA GTGAGGAGGC TTTTTTGGAG GCCTAGGCTT TTGCAAAAAG C TCCTCCGAT     360

CGAGGGGCTC GCATCTCTCC TTCACGCGCC CGCCGCCCTA CCTGAGGCCG C CATCCACGC     420

CGGTTGAGTC GCGTTCTGCC GCCTCCCGCC TGTGGTGCCT CCTGAACTGC G TCCGCCGTC     480
```

-continued

```
TAGGTAAGTT TAAAGCTCAG GTCGAGACCG GGCCTTTGTC CGGCGCTCCC T TGGAGCCTA      540

CCTAGACTCA GCCGGCTCTC CACGCTTTGC CTGACCCTGC TTGCTCAACT C TACGTCTTT      600

GTTTCGTTTT CTGTTCTGCG CCGTTACAGA TCCAAGCTCT GAAAAACCAG A AAGTTAACT      660

GGTAAGTTTA GTCTTTTTGT CTTTTATTTC AGGTCCCAGG TCCCGGATCC G GTGATCCAA      720

ATCTAAGAAC TGCTCCTCAG TGAGTGTTGC CTTTACTTCT AGGCCTGTAC G GAAGTGTTA      780

CTTCTGCTCT AAAAGCTGCG GAATTCGCAC CACCGTAGTT TTTACGCCCG G TGAGCGCTC      840

CACCCGCACC TACAAGCGCG TGTATGATGA GGTGTACGGC GACGAGGACC T GCTTGAGCA      900

GGCCAACGAG CGCCTCGGGG AGTTTGCCTA CGGAAAGCGG CATAAGGACA T GTTGGCGTT      960

GCCGCTGGAC GAGGGCAACC CAACACCTAG CCTAAAGCCC GTGACACTGC A GCAGGTGCT     1020

GCCCACGCTT GCACCGTCCG AAGAAAAGCG CGGCCTAAAG CGCGAGTCTG G TGACTTGGC     1080

ACCCACCGTG CAGCTGATGG TACCCAAGCG CCAGCGACTG GAAGATGTCT T GGAAAAAAT     1140

GACCGTGGAG CCTGGGCTGG AGCCCGAGGT CCGCGTGCGG CCAATCAAGC A GGTGGCACC     1200

GGGACTGGGC GTGCAGACCG TGGACGTTCA GATACCCACC ACCAGTAGCA C TAGTATTGC     1260

CACTGCCACA GAGGGCATGG AGACACAAAC GTCCCCGGTT GCCTAGCTCG A GATCATCCC     1320

AGTTGAGGAG GAGAACCCGG ACTTCTGGAA CCGCGAGGCA GCCGAGGCCC T GGGTGCCGC     1380

CAAGAAGCTG CAGCCTGCAC AGACAGCCGC CAAGAACCTC ATCATCTTCC T GGGCGATGG     1440

GATGGGGGTG TCTACGGTGA CAGCTGCCAG GATCCTAAAA GGGCAGAAGA A GGACAAACT     1500

GGGGCCTGAG ATACCCCTGG CCATGGACCG CTTCCCATAT GTGGCTCTGT C CAAGACATA     1560

CAATGTAGAC AAACATGTGC CAGACAGTGG AGCCACAGCC ACGGCCTACC T GTGCGGGGT     1620

CAAGGGCAAC TTCCAGACCA TTGGCTTGAG TGCAGCCGCC CGCTTTAACC A GTGCAACAC     1680

GACACGCGGC AACGAGGTCA CTCCGTGAT GAATCGGGCC AAGAAAGCAG G GAAGTCAGT     1740

GGGAGTGGTA ACCACCACAC GAGTGCAGCA CGCCTCGCCA GCCGGCACCT A CGCCCACAC     1800

GGTGAACCGC AACTGGTACT CGGACGCCGA CGTGCCTGCC TCGGCCCGCC A GGAGGGGTG     1860

CCAGGACATC GCTACGCAGC TCATCTCCAA CATGGACATT GACGTGATCC T AGGTGGAGG     1920

CCGAAAGTAC ATGTTTCGCA TGGGAACCCC AGACCCTGAG TACCCAGATG A CTACAGCCA     1980

AGGTGGGACC AGGCTGGACG GGAAGAATCT GGTGCAGGAA TGGCTGGCGA A GCGCCAGGG     2040

TGCCCGGTAT GTGTGGAACC GCACTGAGCT CATGCAGGCT TCCCTGGACC C GTCTGTGAC     2100

CCATCTCATG GGTCTCTTTG AGCCTGGAGA CATGAAATAC GAGATCCACC G AGACTCCAC     2160

ACTGGACCCC TCCCTGATGG AGATGACAGA GGCTGCCCTG CGCCTGCTGA G CAGGAACCC     2220

CCGCGGCTTC TTCCTCTTCG TGGAGGGTGG TCGCATCGAC CATGGTCATC A TGAAAGCAG     2280

GGCTTACCGG GCACTGACTG AGACGATCAT GTTCGACGAC GCCATTGAGA G GGCGGGCCA     2340

GCTCACCAGC GAGGAGGACA CGCTGAGCCT CGTCACTGCC GACCACTCCC A CGTCTTCTC     2400

CTTCGGAGGC TACCCCCTGC GAGGGAGCTC CATCTTCGGG CTGGCCCCTG G CAAGGCCCG     2460

GGACAGGAAG GCCTACACGG TCCTCCTATA CGGAAACGGT CCAGGCTATG T GCTCAAGGA     2520

CGGCGCCCGG CCGGATGTTA CCGAGAGCGA GAGCGGGAGC CCCGAGTATC G GCAGCAGTC     2580

AGCAGTGCCC CTGGACGAAG AGACCCACGC AGGCGAGGAC GTGGCGGTGT T CGCGCGCGG     2640

CCCGCAGGCG CACCTGGTTC ACGGCGTGCA GGAGCAGACC TTCATAGCGC A CGTCATGGC     2700

CTTCGCCGCC TGCCTGGAGC CCTACACCGC CTGCGACCTG GCGCCCCCG C CGGCACCAC     2760

CGACGCCGCG CACCCGGGTT GAACTAGTCT AGAGAAAAAA CCTCCCACAC C TCCCCCTGA     2820

ACCTGAAACA TAAAATGAAT GCAATTGTTG TTGTTAACTT GTTTATTGCA G CTTATAATG     2880
```

```
GTTACAAATA AAGCAATAGC ATCACAAATT TCACAAATAA AGCATTTTTT T CACTGCATT    2940

CTAGTTGTGG TTTGTCCAAA CTCATCAATG TATCTTATCA TGTCTGGATC C CCGGGTACC    3000

GAGCTCGAAT TAATTCCTCT TCCGCTTCCT CGCTCACTGA CTCGCTGCGC T CGGTCGTTC    3060

GGCTGCGGCG AGCGGTATCA GCTCACTCAA AGGCGGTAAT ACGGTTATCC A CAGAATCAG    3120

GGGATAACGC AGGAAAGAAC ATGTGAGCAA AAGGCCAGCA AAAGGCCAGG A ACCGTAAAA    3180

AGGCCGCGTT GCTGGCGTTT TTCCATAGGC TCCGCCCCCC TGACGAGCAT C ACAAAAATC    3240

GACGCTCAAG TCAGAGGTGG CGAAACCCGA CAGGACTATA AAGATACCAG G CGTTTCCCC    3300

CTGGAAGCTC CCTCGTGCGC TCTCCTGTTC CGACCCTGCC GCTTACCGGA T ACCTGTCCG    3360

CCTTTCTCCC TTCGGGAAGC GTGGCGCTTT CTCAATGCTC ACGCTGTAGG T ATCTCAGTT    3420

CGGTGTAGGT CGTTCGCTCC AAGCTGGGCT GTGTGCACGA ACCCCCCGTT C AGCCCGACC    3480

GCTGCGCCTT ATCCGGTAAC TATCGTCTTG AGTCCAACCC GGTAAGACAC G ACTTATCGC    3540

CACTGGCAGC AGCCACTGGT AACAGGATTA GCAGAGCGAG GTATGTAGGC G GTGCTACAG    3600

AGTTCTTGAA GTGGTGGCCT AACTACGGCT ACACTAGAAG GACAGTATTT G GTATCTGCG    3660

CTCTGCTGAA GCCAGTTACC TTCGGAAAAA GAGTTGGTAG CTCTTGATCC G GCAAACAAA    3720

CCACCGCTGG TAGCGGTGGT TTTTTTGTTT GCAAGCAGCA GATTACGCGC A GAAAAAAAG    3780

GATCTCAAGA AGATCCTTTG ATCTTTTCTA CGGGGTCTGA CGCTCAGTGG A ACGAAAACT    3840

CACGTTAAGG GATTTTGGTC ATGAGATTAT CAAAAAGGAT CTTCACCTAG A TCCTTTTAA    3900

ATTAAAAATG AAGTTTTAAA TCAATCTAAA GTATATATGA GTAAACTTGG T CTGACAGTT    3960

ACCAATGCTT AATCAGTGAG GCACCTATCT CAGCGATCTG TCTATTTCGT T CATCCATAG    4020

TTGCCTGACT CCCCGTCGTG TAGATAACTA CGATACGGGA GGGCTTACCA T CTGGCCCCA    4080

GTGCTGCAAT GATACCGCGA GACCCACGCT CACCGGCTCC AGATTTATCA G CAATAAACC    4140

AGCCAGCCGG AAGGGCCGAG CGCAGAAGTG GTCCTGCAAC TTTATCCGCC T CCATCCAGT    4200

CTATTAATTG TTGCCGGGAA GCTAGAGTAA GTAGTTCGCC AGTTAATAGT T TGCGCAACG    4260

TTGTTGCCAT TGCTACAGGC ATCGTGGTGT CACGCTCGTC GTTTGGTATG G CTTCATTCA    4320

GCTCCGGTTC CCAACGATCA AGGCGAGTTA CATGATCCCC CATGTTGTGC A AAAAAGCGG    4380

TTAGCTCCTT CGGTCCTCCG ATCGTTGTCA GAAGTAAGTT GGCCGCAGTG T TATCACTCA    4440

TGGTTATGGC AGCACTGCAT AATTCTCTTA CTGTCATGCC ATCCGTAAGA T GCTTTTCTG    4500

TGACTGGTGA GTACTCAACC AAGTCATTCT GAGAATAGTG TATGCGGCGA C CGAGTTGCT    4560

CTTGCCCGGC GTCAATACGG GATAATACCG CGCCACATAG CAGAACTTTA A AAGTGCTCA    4620

TCATTGGAAA ACGTTCTTCG GGGCGAAAAC TCTCAAGGAT CTTACCGCTG T TGAGATCCA    4680

GTTCGATGTA ACCCACTCGT GCACCCAACT GATCTTCAGC ATCTTTTACT T TCACCAGCG    4740

TTTCTGGGTG AGCAAAAACA GGAAGGCAAA ATGCCGCAAA AAAGGGAATA A GGGCGACAC    4800

GGAAATGTTG AATACTCATA CTCTTCCTTT TTCAATATTA TTGAAGCATT T ATCAGGGTT    4860

ATTGTCTCAT GAGCGGATAC ATATTTGAAT GTATTTAGAA AAATAAACAA A TAGGGGTTC    4920

CGCGCACATT TCCCCGAAAA GTGCCACCTG C                                    4951
```

(2) INFORMATION FOR SEQ ID NO: 2:

(i) SEQUENCE CHARACTERISTICS:
        (A) LENGTH: 530 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Leu Leu Leu Leu Leu Leu Gly Leu Arg Leu Gln Leu Ser Leu
 1               5                  10                  15

Gly Ile Ile Pro Val Glu Glu Asn Pro Asp Phe Trp Asn Arg Glu
                20                  25                  30

Ala Ala Glu Ala Leu Gly Ala Ala Lys Lys Leu Gln Pro Ala Gln Thr
            35                  40                  45

Ala Ala Lys Asn Leu Ile Ile Phe Leu Gly Asp Gly Met Gly Val Ser
         50                  55                  60

Thr Val Thr Ala Ala Arg Ile Leu Lys Gly Gln Lys Lys Asp Lys Leu
 65                  70                  75                  80

Gly Pro Glu Ile Pro Leu Ala Met Asp Arg Phe Pro Tyr Val Ala Leu
                    85                  90                  95

Ser Lys Thr Tyr Asn Val Asp Lys His Val Pro Asp Ser Gly Ala Thr
            100                 105                 110

Ala Thr Ala Tyr Leu Cys Gly Val Lys Gly Asn Phe Gln Thr Ile Gly
            115                 120                 125

Leu Ser Ala Ala Ala Arg Phe Asn Gln Cys Asn Thr Thr Arg Gly Asn
130                 135                 140

Glu Val Ile Ser Val Met Asn Arg Ala Lys Lys Ala Gly Lys Ser Val
145                 150                 155                 160

Gly Val Val Thr Thr Thr Arg Val Gln His Ala Ser Pro Ala Gly Thr
                    165                 170                 175

Tyr Ala His Thr Val Asn Arg Asn Trp Tyr Ser Asp Ala Asp Val Pro
            180                 185                 190

Ala Ser Ala Arg Gln Glu Gly Cys Gln Asp Ile Ala Thr Gln Leu Ile
        195                 200                 205

Ser Asn Met Asp Ile Asp Val Ile Leu Gly Gly Gly Arg Lys Tyr Met
210                 215                 220

Phe Arg Met Gly Thr Pro Asp Pro Glu Tyr Pro Asp Asp Tyr Ser Gln
225                 230                 235                 240

Gly Gly Thr Arg Leu Asp Gly Lys Asn Leu Val Gln Glu Trp Leu Ala
                245                 250                 255

Lys Arg Gln Gly Ala Arg Tyr Val Trp Asn Arg Thr Glu Leu Met Gln
                260                 265                 270

Ala Ser Leu Asp Pro Ser Val Thr His Leu Met Gly Leu Phe Glu Pro
            275                 280                 285

Gly Asp Met Lys Tyr Glu Ile His Arg Asp Ser Thr Leu Asp Pro Ser
290                 295                 300

Leu Met Glu Met Thr Glu Ala Ala Leu Arg Leu Leu Ser Arg Asn Pro
305                 310                 315                 320

Arg Gly Phe Phe Leu Phe Val Glu Gly Gly Arg Ile Asp His Gly His
                325                 330                 335

His Glu Ser Arg Ala Tyr Arg Ala Leu Thr Glu Thr Ile Met Phe Asp
            340                 345                 350

Asp Ala Ile Glu Arg Ala Gly Gln Leu Thr Ser Glu Glu Asp Thr Leu
            355                 360                 365

Ser Leu Val Thr Ala Asp His Ser His Val Phe Ser Phe Gly Gly Tyr
370                 375                 380

Pro Leu Arg Gly Ser Ser Ile Phe Gly Leu Ala Pro Gly Lys Ala Arg
385                 390                 395                 400
```

```
Asp Arg Lys Ala Tyr Thr Val Leu Leu Tyr Gly Asn Gly Pro Gly Tyr
                405                 410                 415

Val Leu Lys Asp Gly Ala Arg Pro Asp Val Thr Glu Ser Glu Ser Gly
                420                 425                 430

Ser Pro Glu Tyr Arg Gln Gln Ser Ala Val Pro Leu Asp Glu Glu Thr
                435                 440                 445

His Ala Gly Glu Asp Val Ala Val Phe Ala Arg Gly Pro Gln Ala His
                450                 455                 460

Leu Val His Gly Val Gln Glu Gln Thr Phe Ile Ala His Val Met Ala
465                 470                 475                 480

Phe Ala Ala Cys Leu Glu Pro Tyr Thr Ala Cys Asp Leu Ala Pro Pro
                485                 490                 495

Ala Gly Thr Thr Asp Ala Ala His Pro Gly Arg Ser Val Val Pro Ala
                500                 505                 510

Leu Leu Pro Leu Leu Ala Gly Thr Leu Leu Leu Leu Glu Thr Ala Thr
                515                 520                 525

Ala Pro
    530

(2) INFORMATION FOR SEQ ID NO: 3:

(i) SEQUENCE CHARACTERISTICS:
        (A) LENGTH: 489 amino acids
        (B) TYPE: amino acid
        (D) TOPOLOGY: linear (ii) MOLECULE TYPE: protein (xi) SEQUENCE DESCRIPTION: SEQ ID NO: 3:

Ile Ile Pro Val Glu Glu Asn Pro Asp Phe Trp Asn Arg Glu Ala
1                5                  10                  15

Ala Glu Ala Leu Gly Ala Ala Lys Lys Leu Gln Pro Ala Gln Thr Ala
                20                  25                  30

Ala Lys Asn Leu Ile Ile Phe Leu Gly Asp Gly Met Gly Val Ser Thr
                35                  40                  45

Val Thr Ala Ala Arg Ile Leu Lys Gly Gln Lys Lys Asp Lys Leu Gly
    50                  55                  60

Pro Glu Ile Pro Leu Ala Met Asp Arg Phe Pro Tyr Val Ala Leu Ser
65                  70                  75                  80

Lys Thr Tyr Asn Val Asp Lys His Val Pro Asp Ser Gly Ala Thr Ala
                85                  90                  95

Thr Ala Tyr Leu Cys Gly Val Lys Gly Asn Phe Gln Thr Ile Gly Leu
                100                 105                 110

Ser Ala Ala Ala Arg Phe Asn Gln Cys Asn Thr Thr Arg Gly Asn Glu
                115                 120                 125

Val Ile Ser Val Met Asn Arg Ala Lys Lys Ala Gly Lys Ser Val Gly
    130                 135                 140

Val Val Thr Thr Thr Arg Val Gln His Ala Ser Pro Ala Gly Thr Tyr
145                 150                 155                 160

Ala His Thr Val Asn Arg Asn Trp Tyr Ser Asp Ala Asp Val Pro Ala
                165                 170                 175

Ser Ala Arg Gln Glu Gly Cys Gln Asp Ile Ala Thr Gln Leu Ile Ser
                180                 185                 190

Asn Met Asp Ile Asp Val Ile Leu Gly Gly Gly Arg Lys Tyr Met Phe
                195                 200                 205

Arg Met Gly Thr Pro Asp Pro Glu Tyr Pro Asp Asp Tyr Ser Gln Gly
```

```
         210                 215                 220
Gly Thr Arg Leu Asp Gly Lys Asn Leu Val G ln Glu Trp Leu Ala Lys
225                 230                 235                 240

Arg Gln Gly Ala Arg Tyr Val Trp Asn Arg T hr Glu Leu Met Gln Ala
                245                 250                 255

Ser Leu Asp Pro Ser Val Thr His Leu Met G ly Leu Phe Glu Pro Gly
                260                 265                 270

Asp Met Lys Tyr Glu Ile His Arg Asp Ser T hr Leu Asp Pro Ser Leu
                275                 280                 285

Met Glu Met Thr Glu Ala Ala Leu Arg Leu L eu Ser Arg Asn Pro Arg
                290                 295                 300

Gly Phe Phe Leu Phe Val Glu Gly Gly Arg I le Asp His Gly His His
305                 310                 315                 320

Glu Ser Arg Ala Tyr Arg Ala Leu Thr Glu T hr Ile Met Phe Asp Asp
                325                 330                 335

Ala Ile Glu Arg Ala Gly Gln Leu Thr Ser G lu Glu Asp Thr Leu Ser
                340                 345                 350

Leu Val Thr Ala Asp His Ser His Val Phe S er Phe Gly Gly Tyr Pro
                355                 360                 365

Leu Arg Gly Ser Ser Ile Phe Gly Leu Ala P ro Gly Lys Ala Arg Asp
370                 375                 380

Arg Lys Ala Tyr Thr Val Leu Leu Tyr Gly A sn Gly Pro Gly Tyr Val
385                 390                 395                 400

Leu Lys Asp Gly Ala Arg Pro Asp Val Thr G lu Ser Glu Ser Gly Ser
                405                 410                 415

Pro Glu Tyr Arg Gln Gln Ser Ala Val Pro L eu Asp Glu Glu Thr His
                420                 425                 430

Ala Gly Glu Asp Val Ala Val Phe Ala Arg G ly Pro Gln Ala His Leu
                435                 440                 445

Val His Gly Val Gln Glu Gln Thr Phe Ile A la His Val Met Ala Phe
                450                 455                 460

Ala Ala Cys Leu Glu Pro Tyr Thr Ala Cys A sp Leu Ala Pro Pro Ala
465                 470                 475                 480

Gly Thr Thr Asp Ala Ala His Pro Gly
                485

(2) INFORMATION FOR SEQ ID NO: 4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 4:

CTGGACTCGA GNNNNNN                                                          17

(2) INFORMATION FOR SEQ ID NO: 5:

(i) SEQUENCE CHARACTERISTICS:
        (A) LENGTH: 465 amino acids
        (B) TYPE: amino acid
        (D) TOPOLOGY: linear (ii) MOLECULE TYPE: protein (v) FRAGMENT TYPE: internal
```

(xi) SEQUENCE DESCRIPTION: SEQ ID NO: 5:

Met Trp Leu Val Thr Phe Leu Leu Leu Asp Ser Leu His Lys Ala
1               5                   10                  15

Arg Pro Glu Asp Val Gly Thr Ser Leu Tyr Phe Val Asn Asp Ser Leu
            20                  25                  30

Gln Gln Val Thr Phe Ser Ser Val Gly Val Val Val Pro Cys Pro
        35                  40                  45

Ala Ala Gly Ser Pro Ser Ala Ala Leu Arg Trp Tyr Leu Ala Thr Gly
        50                  55                  60

Asp Asp Ile Tyr Asp Val Pro His Ile Arg His Val His Ala Asn Gly
65                  70                  75                  80

Thr Leu Gln Leu Tyr Pro Phe Ser Pro Ser Ala Phe Asn Ser Phe Ile
                85                  90                  95

His Asp Asn Asp Tyr Phe Cys Thr Ala Glu Asn Ala Ala Gly Lys Ile
                100                 105                 110

Arg Ser Pro Asn Ile Arg Val Lys Ala Val Phe Arg Glu Pro Tyr Thr
        115                 120                 125

Val Arg Val Glu Asp Gln Arg Ser Met Arg Gly Asn Val Ala Val Phe
    130                 135                 140

Lys Cys Leu Ile Pro Ser Ser Val Gln Glu Tyr Val Ser Val Ser
145                 150                 155                 160

Trp Glu Lys Asp Thr Val Ser Ile Ile Pro Glu Asn Arg Phe Phe Ile
                165                 170                 175

Thr Tyr His Gly Gly Leu Tyr Ile Ser Asp Val Gln Lys Glu Asp Ala
                180                 185                 190

Leu Ser Thr Tyr Arg Cys Ile Thr Lys His Lys Tyr Ser Gly Glu Thr
        195                 200                 205

Arg Gln Ser Asn Gly Ala Arg Leu Ser Val Thr Asp Pro Ala Glu Ser
    210                 215                 220

Ile Pro Thr Ile Leu Asp Gly Phe His Ser Gln Glu Val Trp Ala Gly
225                 230                 235                 240

His Thr Val Glu Leu Pro Cys Thr Ala Ser Gly Tyr Pro Ile Pro Ala
                245                 250                 255

Ile Arg Trp Leu Lys Asp Gly Arg Pro Leu Pro Ala Asp Ser Arg Trp
                260                 265                 270

Thr Lys Arg Ile Thr Gly Leu Thr Ile Ser Asp Leu Arg Thr Glu Asp
        275                 280                 285

Ser Gly Thr Tyr Ile Cys Glu Val Thr Asn Thr Phe Gly Ser Ala Glu
    290                 295                 300

Ala Thr Gly Ile Leu Met Val Ile Asp Pro Leu His Val Thr Leu Thr
305                 310                 315                 320

Pro Lys Lys Leu Lys Thr Gly Ile Gly Ser Thr Val Ile Leu Ser Cys
                325                 330                 335

Ala Leu Thr Gly Ser Pro Glu Phe Thr Ile Arg Trp Tyr Arg Asn Thr
                340                 345                 350

Glu Leu Val Leu Pro Asp Glu Ala Ile Ser Ile Arg Gly Leu Ser Asn
        355                 360                 365

Glu Thr Leu Leu Ile Thr Ser Ala Gln Lys Ser His Ser Gly Ala Tyr
    370                 375                 380

Gln Cys Phe Ala Thr Arg Lys Ala Gln Thr Ala Gln Asp Phe Ala Ile
385                 390                 395                 400

Ile Ala Leu Glu Asp Gly Thr Pro Arg Ile Val Ser Ser Phe Ser Glu

```
                     405                 410                 415
Lys Val Val Asn Pro Gly Glu Gln Phe Ser L eu Met Cys Ala Ala Lys
                420                 425                 430
Gly Ala Pro Pro Thr Val Thr Trp Ala L eu Asp Asp Glu Pro Ile
            435                 440                 445
Val Arg Asp Gly Ser His Arg Thr Asn Gln T yr Thr Met Ser Asp Gly
    450                 455                 460
Thr
465

(2) INFORMATION FOR SEQ ID NO: 6:

(i) SEQUENCE CHARACTERISTICS:
        (A) LENGTH: 1493 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding S equence
        (B) LOCATION: 99...1493

(xi) SEQUENCE DESCRIPTION: SEQ ID NO: 6:

GGCACGAGGG CGGCTGGGAG CGCGCTGAGC GGGGGAGAGG CGCTGCCGCA C GGCCGGCCA        60

CAGGACCACC TCCCCGGAGA ATAGGGCCTC TTTATGGC ATG TGG CTG  GTA ACT TTC      116
                                           Met Trp Leu Val Thr Phe
                                             1                   5

CTC CTG CTC CTG GAC TCT TTA CAC AAA GCC C GC CCT GAA GAT GTT GGC        164
Leu Leu Leu Leu Asp Ser Leu His Lys Ala A rg Pro Glu Asp Val Gly
                 10                  15                  20

ACC AGC CTC TAC TTT GTA AAT GAC TCC TTG C AG CAG GTG ACC TTT TCC        212
Thr Ser Leu Tyr Phe Val Asn Asp Ser Leu G ln Gln Val Thr Phe Ser
            25                  30                  35

AGC TCC GTG GGG GTG GTG GTG CCC TGC CCG G CC GCG GGC TCC CCC AGC        260
Ser Ser Val Gly Val Val Val Pro Cys Pro A la Ala Gly Ser Pro Ser
    40                  45                  50

GCG GCC CTT CGA TGG TAC CTG GCC ACA GGG G AC GAC ATC TAC GAC GTG        308
Ala Ala Leu Arg Trp Tyr Leu Ala Thr Gly A sp Asp Ile Tyr Asp Val
55                  60                  65                  70

CCG CAC ATC CGG CAC GTC CAC GCC AAC GGG A CG CTG CAG CTC TAC CCC        356
Pro His Ile Arg His Val His Ala Asn Gly T hr Leu Gln Leu Tyr Pro
                 75                  80                  85

TTC TCC CCC TCC GCC TTC AAT AGC TTT ATC C AC GAC AAT GAC TAC TTC        404
Phe Ser Pro Ser Ala Phe Asn Ser Phe Ile H is Asp Asn Asp Tyr Phe
            90                  95                 100

TGC ACC GCG GAG AAC GCT GCC GGC AAG ATC C GG AGC CCC AAC ATC CGC        452
Cys Thr Ala Glu Asn Ala Ala Gly Lys Ile A rg Ser Pro Asn Ile Arg
    105                 110                 115

GTC AAA GCA GTT TTC AGG GAA CCC TAC ACC G TC CGG GTG GAG GAT CAA        500
Val Lys Ala Val Phe Arg Glu Pro Tyr Thr V al Arg Val Glu Asp Gln
120                 125                 130

AGG TCA ATG CGT GGC AAC GTG GCC GTC TTC A AG TGC CTC ATC CCC TCT        548
Arg Ser Met Arg Gly Asn Val Ala Val Phe L ys Cys Leu Ile Pro Ser
135                 140                 145                 150

TCA GTG CAG GAA TAT GTT AGC GTT GTA TCT T GG GAG AAA GAC ACA GTC        596
Ser Val Gln Glu Tyr Val Ser Val Val Ser T rp Glu Lys Asp Thr Val
                155                 160                 165

TCC ATC ATC CCA GAA AAC AGG TTT TTT ATT A CC TAC CAC GGC GGG CTG        644
Ser Ile Ile Pro Glu Asn Arg Phe Phe Ile T hr Tyr His Gly Gly Leu
```

|   |   |   |   |   |   |   |   |   |   |   |
|---|---|---|---|---|---|---|---|---|---|---|
|   |   | 170 |   |   | 175 |   |   | 180 |   |   |
| TAC | ATC | TCT | GAC | GTA | CAG | AAG | GAG | GAC | GCC | C TC TCC ACC TAT CGC TGC | 692 |
| Tyr | Ile | Ser | Asp | Val | Gln | Lys | Glu | Asp | Ala | L eu Ser Thr Tyr Arg Cys |
|   |   | 185 |   |   | 190 |   |   | 195 |   |   |
| ATC | ACC | AAG | CAC | AAG | TAT | AGC | GGG | GAG | ACC | C GG CAG AGC AAT GGG GCA | 740 |
| Ile | Thr | Lys | His | Lys | Tyr | Ser | Gly | Glu | Thr | A rg Gln Ser Asn Gly Ala |
|   |   | 200 |   |   | 205 |   |   | 210 |   |   |
| CGC | CTC | TCT | GTG | ACA | GAC | CCT | GCT | GAG | TCG | A TC CCC ACC ATC CTG GAT | 788 |
| Arg | Leu | Ser | Val | Thr | Asp | Pro | Ala | Glu | Ser | I le Pro Thr Ile Leu Asp |
| 215 |   |   |   | 220 |   |   |   | 225 |   | 230 |
| GGC | TTC | CAC | TCC | CAG | GAA | GTG | TGG | GCC | GGC | C AC ACC GTG GAG CTG CCC | 836 |
| Gly | Phe | His | Ser | Gln | Glu | Val | Trp | Ala | Gly | H is Thr Val Glu Leu Pro |
|   |   |   | 235 |   |   |   | 240 |   |   | 245 |
| TGC | ACC | GCC | TCG | GGC | TAC | CCT | ATC | CCC | GCC | A TC CGC TGG CTC AAG GAT | 884 |
| Cys | Thr | Ala | Ser | Gly | Tyr | Pro | Ile | Pro | Ala | I le Arg Trp Leu Lys Asp |
|   |   |   | 250 |   |   |   | 255 |   |   | 260 |
| GGC | CGG | CCC | CTC | CCG | GCT | GAC | AGC | CGC | TGG | A CC AAG CGC ATC ACA GGG | 932 |
| Gly | Arg | Pro | Leu | Pro | Ala | Asp | Ser | Arg | Trp | T hr Lys Arg Ile Thr Gly |
|   |   | 265 |   |   |   | 270 |   |   |   | 275 |
| CTG | ACC | ATC | AGC | GAC | TTG | CGG | ACC | GAG | GAC | A GC GGC ACC TAC ATT TGT | 980 |
| Leu | Thr | Ile | Ser | Asp | Leu | Arg | Thr | Glu | Asp | S er Gly Thr Tyr Ile Cys |
|   |   | 280 |   |   |   | 285 |   |   |   | 290 |
| GAG | GTC | ACC | AAC | ACC | TTC | GGT | TCG | GCA | GAG | G CC ACA GGC ATC CTC ATG | 1028 |
| Glu | Val | Thr | Asn | Thr | Phe | Gly | Ser | Ala | Glu | A la Thr Gly Ile Leu Met |
| 295 |   |   |   | 300 |   |   |   | 305 |   | 310 |
| GTC | ATT | GAT | CCC | CTT | CAT | GTG | ACC | CTG | ACA | C CA AAG AAG CTG AAG ACC | 1076 |
| Val | Ile | Asp | Pro | Leu | His | Val | Thr | Leu | Thr | P ro Lys Lys Leu Lys Thr |
|   |   |   | 315 |   |   |   | 320 |   |   | 325 |
| GGC | ATT | GGC | AGC | ACG | GTC | ATC | CTC | TCC | TGT | G CC CTG ACG GGC TCC CCA | 1124 |
| Gly | Ile | Gly | Ser | Thr | Val | Ile | Leu | Ser | Cys | A la Leu Thr Gly Ser Pro |
|   |   |   | 330 |   |   |   | 335 |   |   | 340 |
| GAG | TTC | ACC | ATC | CGC | TGG | TAT | CGC | AAC | ACG | G AG CTG GTG CTG CCT GAC | 1172 |
| Glu | Phe | Thr | Ile | Arg | Trp | Tyr | Arg | Asn | Thr | G lu Leu Val Leu Pro Asp |
|   |   |   | 345 |   |   |   | 350 |   |   | 355 |
| GAG | GCC | ATC | TCC | ATC | CGT | GGG | CTC | AGC | AAC | G AG ACG CTG CTC ATC ACC | 1220 |
| Glu | Ala | Ile | Ser | Ile | Arg | Gly | Leu | Ser | Asn | G lu Thr Leu Leu Ile Thr |
|   |   | 360 |   |   |   | 365 |   |   |   | 370 |
| TCG | GCC | CAG | AAG | AGC | CAT | TCC | GGG | GCC | TAC | C AG TGC TTC GCT ACC CGC | 1268 |
| Ser | Ala | Gln | Lys | Ser | His | Ser | Gly | Ala | Tyr | G ln Cys Phe Ala Thr Arg |
| 375 |   |   |   | 380 |   |   |   | 385 |   | 390 |
| AAG | GCC | CAG | ACC | GCC | CAG | GAC | TTT | GCC | ATC | A TT GCA CTT GAG GAT GGC | 1316 |
| Lys | Ala | Gln | Thr | Ala | Gln | Asp | Phe | Ala | Ile | I le Ala Leu Glu Asp Gly |
|   |   |   | 395 |   |   |   | 400 |   |   | 405 |
| ACG | CCC | CGC | ATC | GTC | TCG | TCC | TTC | AGC | GAG | A AG GTG GTC AAC CCC GGG | 1364 |
| Thr | Pro | Arg | Ile | Val | Ser | Ser | Phe | Ser | Glu | L ys Val Val Asn Pro Gly |
|   |   |   | 410 |   |   |   | 415 |   |   | 420 |
| GAG | CAG | TTC | TCA | CTG | ATG | TGT | GCG | GCC | AAG | G GC GCC CCG CCC CCC ACG | 1412 |
| Glu | Gln | Phe | Ser | Leu | Met | Cys | Ala | Ala | Lys | G ly Ala Pro Pro Pro Thr |
|   |   | 425 |   |   |   | 430 |   |   |   | 435 |
| GTC | ACC | TGG | GCC | CTC | GAC | GAT | GAG | CCC | ATC | G TG CGG GAT GGC AGC CAC | 1460 |
| Val | Thr | Trp | Ala | Leu | Asp | Asp | Glu | Pro | Ile | V al Arg Asp Gly Ser His |
|   |   | 440 |   |   |   | 445 |   |   |   | 450 |
| CGC | ACC | AAC | CAG | TAC | ACC | ATG | TCG | GAC | GGC | A CC | 1493 |
| Arg | Thr | Asn | Gln | Tyr | Thr | Met | Ser | Asp | Gly | T hr |
| 455 |   |   |   | 460 |   |   |   | 465 |   |   |

(2) INFORMATION FOR SEQ ID NO: 7:

(i) SEQUENCE CHARACTERISTICS:
        (A) LENGTH: 462 amino acids (B) TYPE: amino acid
        (D) TOPOLOGY: linear (ii) MOLECULE TYPE: protein (xi) SEQUENCE DESCRIPTION: SEQ ID NO: 7:

```
Met Trp Leu Val Thr Phe Leu Leu Leu Asp Ser Leu His Lys Ala
 1               5                  10                  15

Arg Pro Glu Asp Val Gly Thr Ser Leu Tyr Phe Val Asn Asp Ser Leu
             20                  25                  30

Gln Gln Val Thr Phe Ser Ser Val Gly Val Val Pro Cys Pro
             35                  40                  45

Ala Ala Gly Ser Pro Ser Ala Ala Leu Arg Trp Tyr Leu Ala Thr Gly
 50                  55                  60

Asp Asp Ile Tyr Asp Val Pro His Ile Arg His Val His Ala Asn Gly
 65                  70                  75                  80

Thr Leu Gln Leu Tyr Pro Phe Ser Pro Ser Ala Phe Asn Ser Phe Ile
                 85                  90                  95

His Asp Asn Asp Tyr Phe Cys Thr Ala Glu Asn Ala Ala Gly Lys Ile
                100                 105                 110

Arg Ser Pro Asn Ile Arg Val Lys Ala Val Phe Arg Glu Pro Tyr Thr
            115                 120                 125

Val Arg Val Glu Asp Gln Arg Ser Met Arg Gly Asn Val Ala Val Phe
130                 135                 140

Lys Cys Leu Ile Pro Ser Ser Val Gln Glu Tyr Val Ser Val Ser
145                 150                 155                 160

Trp Glu Lys Asp Thr Val Ser Ile Ile Pro Glu Asn Arg Phe Phe Ile
                165                 170                 175

Thr Tyr His Gly Gly Leu Tyr Ile Ser Asp Val Gln Lys Glu Asp Ala
                180                 185                 190

Leu Ser Thr Tyr Arg Cys Ile Thr Lys His Lys Tyr Ser Gly Glu Thr
            195                 200                 205

Arg Gln Ser Asn Gly Ala Arg Leu Ser Val Thr Asp Pro Ala Glu Ser
        210                 215                 220

Ile Pro Thr Ile Leu Asp Gly Phe His Ser Gln Glu Val Trp Ala Gly
225                 230                 235                 240

His Thr Val Glu Leu Pro Cys Thr Ala Ser Gly Tyr Pro Ile Pro Ala
                245                 250                 255

Ile Arg Trp Leu Lys Asp Gly Arg Pro Leu Pro Ala Asp Ser Arg Trp
                260                 265                 270

Thr Lys Arg Ile Thr Gly Leu Thr Ile Ser Asp Leu Arg Thr Glu Asp
        275                 280                 285

Ser Gly Thr Tyr Ile Cys Glu Val Thr Asn Thr Phe Gly Ser Ala Glu
    290                 295                 300

Ala Thr Gly Ile Leu Met Val Ile Asp Pro Leu His Val Thr Leu Thr
305                 310                 315                 320

Pro Lys Lys Leu Lys Thr Gly Ile Gly Ser Thr Val Ile Leu Ser Cys
                325                 330                 335

Ala Leu Thr Gly Ser Pro Glu Phe Thr Ile Arg Trp Tyr Arg Asn Thr
                340                 345                 350

Glu Leu Val Leu Pro Asp Glu Ala Ile Ser Ile Arg Gly Leu Ser Asn
        355                 360                 365

Glu Thr Leu Leu Ile Thr Ser Ala Gln Lys Ser His Ser Gly Ala Tyr
    370                 375                 380
```

```
Gln Cys Phe Ala Thr Arg Lys Ala Gln Thr A la Gln Asp Phe Ala Ile
385                 390                 395                 400

Ile Ala Leu Glu Asp Gly Thr Pro Arg Ile V al Ser Ser Phe Ser Glu
                405                 410                 415

Lys Val Val Asn Pro Gly Glu Gln Phe Ser L eu Met Cys Ala Ala Lys
                420                 425                 430

Gly Ala Pro Pro Thr Val Thr Trp Ala L eu Asp Asp Glu Pro Ile
                435             440                 445

Val Arg Asp Gly Ser His Arg Thr Asn Gln T yr Thr Met Ser
                450                 455                 460
```

(2) INFORMATION FOR SEQ ID NO: 8:

(i) SEQUENCE CHARACTERISTICS:
        (A) LENGTH: 605 amino acids
        (B) TYPE: amino acid
        (D) TOPOLOGY: linear (ii) MOLECULE TYPE: protein (xi) SEQUENCE DESCRIPTION: SEQ ID NO: 8:

```
Met Lys Thr Pro Leu Leu Val Ser His Leu L eu Leu Ile Ser Leu Thr
1               5                   10                  15

Ser Cys Leu Gly Glu Phe Thr Trp His Arg A rg Tyr Gly His Gly Val
                20                  25                  30

Ser Glu Glu Asp Lys Gly Phe Gly Pro Ile P he Glu Glu Gln Pro Ile
            35                  40                  45

Asn Thr Ile Tyr Pro Glu Glu Ser Leu Glu G ly Lys Val Ser Leu Asn
            50                  55                  60

Cys Arg Ala Arg Ala Ser Pro Phe Pro Val T yr Lys Trp Arg Met Asn
65                  70                  75                  80

Asn Gly Asp Val Asp Leu Thr Asn Asp Arg T yr Ser Met Val Gly Gly
                85                  90                  95

Asn Leu Val Ile Asn Asn Pro Asp Lys Gln L ys Asp Ala Gly Ile Tyr
                100                 105                 110

Tyr Cys Leu Ala Ser Asn Asn Tyr Gly Met V al Arg Ser Thr Glu Ala
            115                 120                 125

Thr Leu Ser Phe Gly Tyr Leu Asp Pro Phe P ro Pro Glu Asp Arg Pro
            130                 135                 140

Glu Val Lys Val Lys Glu Gly Lys Gly Met V al Leu Leu Cys Asp Pro
145                 150                 155                 160

Pro Tyr His Phe Pro Asp Asp Leu Ser Tyr A rg Trp Leu Leu Asn Glu
                165                 170                 175

Phe Pro Val Phe Ile Thr Met Asp Lys Arg A rg Phe Val Ser Gln Thr
                180                 185                 190

Asn Gly Asn Leu Tyr Ile Ala Asn Val Glu S er Ser Asp Arg Gly Asn
            195                 200                 205

Tyr Ser Cys Phe Val Ser Ser Pro Ser Ile T hr Lys Ser Val Phe Ser
            210                 215                 220

Lys Phe Ile Pro Leu Ile Pro Ile Pro Glu A rg Thr Thr Lys Pro Tyr
225                 230                 235                 240

Pro Ala Asp Ile Val Val Gln Phe Lys Asp I le Tyr Thr Met Met Gly
                245                 250                 255

Gln Asn Val Thr Leu Glu Cys Phe Ala Leu G ly Asn Pro Val Pro Asp
                260                 265                 270

Ile Arg Trp Arg Lys Val Leu Glu Pro Met P ro Thr Thr Ala Glu Ile
```

```
                   275                 280                     285
Ser Thr Ser Gly Ala Val Leu Lys Ile Phe A sn Ile Gln Leu Glu Asp
            290                 295                300

Glu Gly Leu Tyr Glu Cys Glu Ala Glu Asn I le Arg Gly Lys Asp Lys
305                 310                 315                 320

His Gln Ala Arg Ile Tyr Val Gln Ala Phe P ro Glu Trp Val Glu His
                325                 330                335

Ile Asn Asp Thr Glu Val Asp Ile Gly Ser A sp Leu Tyr Trp Pro Cys
                340                 345                 350

Val Ala Thr Gly Lys Pro Ile Pro Thr Ile A rg Trp Leu Lys Asn Gly
                355                 360                 365

Tyr Ala Tyr His Lys Gly Glu Leu Arg Leu T yr Asp Val Thr Phe Glu
            370                 375                380

Asn Ala Gly Met Tyr Gln Cys Ile Ala Glu A sn Ala Tyr Gly Thr Ile
385                 390                 395                 400

Tyr Ala Asn Ala Glu Leu Lys Ile Leu Ala L eu Ala Pro Thr Phe Glu
                405                 410                 415

Met Asn Pro Met Lys Lys Ile Leu Ala A la Lys Gly Gly Arg Val
                420                 425                 430

Ile Ile Glu Cys Lys Pro Lys Ala Ala Pro L ys Pro Lys Phe Ser Trp
                435                 440                 445

Ser Lys Gly Thr Glu Trp Leu Val Asn Ser S er Arg Ile Leu Ile Trp
450                 455                 460

Glu Asp Gly Ser Leu Glu Ile Asn Asn Ile T hr Arg Asn Asp Gly Gly
465                 470                 475                 480

Ile Tyr Thr Cys Phe Ala Glu Asn Asn Arg G ly Lys Ala Asn Ser Thr
                485                 490                 495

Gly Thr Leu Val Ile Thr Asn Pro Thr Arg I le Ile Leu Ala Pro Ile
                500                 505                 510

Asn Ala Asp Ile Thr Val Gly Glu Asn Ala T hr Met Gln Cys Ala Ala
                515                 520                 525

Ser Phe Asp Pro Ser Leu Asp Leu Thr Phe V al Trp Ser Phe Asn Gly
                530                 535                 540

Tyr Val Ile Asp Phe Asn Lys Glu Ile Thr A sn Ile His Tyr Gln Arg
545                 550                 555                 560

Asn Phe Met Leu Asp Ala Asn Gly Glu Leu L eu Ile Arg Asn Ala Gln
                565                 570                 575

Leu Lys His Ala Gly Arg Tyr Thr Cys Thr A la Gln Thr Ile Val Asp
                580                 585                 590

Asn Ser Ser Ala Ser Ala Asp Leu Val Val A rg Gly Pro
            595                 600                 605

(2) INFORMATION FOR SEQ ID NO: 9:

(i) SEQUENCE CHARACTERISTICS:
        (A) LENGTH: 615 amino acids
        (B) TYPE: amino acid
        (D) TOPOLOGY: linear (ii) MOLECULE TYPE: protein (xi) SEQUENCE DESCRIPTION: SEQ ID NO: 9:

Met Trp Arg Gln Ser Thr Ile Leu Ala Ala L eu Leu Val Ala Leu Leu
1               5                   10                  15

Cys Ala Gly Ser Ala Glu Ser Lys Gly Asn A rg Pro Pro Arg Ile Thr
            20                  25                  30
```

-continued

```
Lys Gln Pro Ala Pro Gly Glu Leu Leu Phe Lys Val Ala Gln Gln Asn
        35                  40                  45
Lys Glu Ser Asp Pro Glu Arg Asn Pro Phe Ile Ile Glu Cys Glu Ala
        50                  55                  60
Asp Gly Gln Pro Glu Pro Glu Tyr Ser Trp Ile Lys Asn Gly Lys Lys
65                      70                  75                  80
Phe Asp Trp Gln Ala Tyr Asp Asn Arg Met Leu Arg Gln Pro Gly Arg
                    85                  90                  95
Gly Thr Leu Val Ile Thr Ile Pro Lys Asp Glu Asp Arg Gly His Tyr
                100                 105                 110
Gln Cys Phe Ala Ser Asn Glu Phe Gly Thr Ala Thr Ser Asn Ser Val
            115                 120                 125
Tyr Val Arg Lys Ala Glu Leu Asn Ala Phe Lys Asp Glu Ala Ala Lys
        130                 135                 140
Thr Leu Glu Ala Val Glu Gly Glu Pro Phe Met Leu Lys Cys Ala Ala
145                 150                 155                 160
Pro Asp Gly Phe Pro Ser Pro Thr Val Asn Trp Met Ile Gln Glu Ser
                165                 170                 175
Ile Asp Gly Ser Ile Lys Ser Ile Asn Asn Ser Arg Met Thr Leu Asp
                180                 185                 190
Pro Glu Gly Asn Leu Trp Phe Ser Asn Val Thr Arg Glu Asp Ala Ser
            195                 200                 205
Ser Asp Phe Tyr Tyr Ala Cys Ser Ala Thr Ser Val Phe Arg Ser Glu
        210                 215                 220
Tyr Lys Ile Gly Asn Lys Val Leu Leu Asp Val Lys Gln Met Gly Val
225                 230                 235                 240
Ser Ala Ser Gln Asn Lys His Pro Pro Val Arg Gln Tyr Val Ser Arg
                245                 250                 255
Arg Gln Ser Ala Leu Arg Gly Lys Arg Met Glu Leu Phe Cys Ile Tyr
            260                 265                 270
Gly Gly Thr Pro Leu Pro Gln Thr Val Trp Ser Lys Asp Gly Gln Arg
        275                 280                 285
Ile Gln Trp Ser Asp Arg Ile Thr Gln Gly His Tyr Gly Lys Ser Leu
        290                 295                 300
Val Ile Arg Gln Thr Asn Phe Asp Asp Ala Gly Thr Tyr Thr Cys Asp
305                 310                 315                 320
Val Ser Asn Gly Val Gly Asn Ala Gln Ser Phe Ser Ile Ile Leu Asn
                325                 330                 335
Val Asn Ser Val Pro Tyr Phe Thr Lys Glu Pro Glu Ile Ala Thr Ala
            340                 345                 350
Ala Glu Asp Glu Glu Val Val Phe Glu Cys Arg Ala Ala Gly Val Pro
        355                 360                 365
Glu Pro Lys Ile Ser Trp Ile His Asn Gly Lys Pro Ile Glu Gln Ser
        370                 375                 380
Thr Pro Asn Pro Arg Arg Thr Val Thr Asp Asn Thr Ile Arg Ile Ile
385                 390                 395                 400
Asn Leu Val Lys Gly Asp Thr Gly Asn Tyr Gly Cys Asn Ala Thr Asn
                405                 410                 415
Ser Leu Gly Tyr Val Tyr Lys Asp Val Tyr Leu Asn Val Gln Ala Glu
            420                 425                 430
Pro Pro Thr Ile Ser Glu Ala Pro Ala Ala Val Ser Thr Val Asp Gly
        435                 440                 445
```

-continued

```
Arg Asn Val Thr Ile Lys Cys Arg Val Asn Gly Ser Pro Lys Pro Leu
    450                 455                 460
Val Lys Trp Leu Arg Ala Ser Asn Trp Leu Thr Gly Gly Arg Tyr Asn
465                 470                 475                 480
Val Gln Ala Asn Gly Asp Leu Glu Ile Gln Asp Val Thr Phe Ser Asp
                485                 490                 495
Ala Gly Lys Tyr Thr Cys Tyr Ala Gln Asn Lys Phe Gly Glu Ile Gln
            500                 505                 510
Ala Asp Gly Ser Leu Val Val Lys Glu His Thr Ile Thr Gln Glu Pro
        515                 520                 525
Gln Asn Tyr Glu Val Ala Ala Gly Gln Ser Ala Thr Phe Arg Cys Asn
    530                 535                 540
Glu Ala His Asp Asp Thr Leu Glu Ile Glu Ile Asp Trp Trp Lys Asp
545                 550                 555                 560
Gly Gln Ser Ile Asp Phe Glu Ala Gln Pro Arg Phe Val Lys Thr Asn
                565                 570                 575
Asp Asn Ser Leu Thr Ile Ala Lys Thr Met Glu Leu Asp Ser Gly Glu
            580                 585                 590
Tyr Thr Cys Val Ala Arg Thr Arg Leu Asp Glu Ala Thr Ala Arg Ala
        595                 600                 605
Asn Leu Ile Val Gln Asp Val
    610                 615

(2) INFORMATION FOR SEQ ID NO: 10:

(i) SEQUENCE CHARACTERISTICS:
        (A) LENGTH: 611 amino acids
        (B) TYPE: amino acid
        (D) TOPOLOGY: linear (ii) MOLECULE TYPE: protein (xi) SEQUENCE DESCRIPTION: SEQ ID NO: 10:

Met Val Val Ala Leu Arg Tyr Val Trp Pro Leu Leu Leu Cys Ser Pro
1               5                   10                  15
Cys Leu Leu Ile Gln Ile Pro Glu Glu Tyr Glu Gly His His Val Met
                20                  25                  30
Glu Pro Pro Val Ile Thr Glu Gln Ser Pro Arg Arg Leu Val Val Phe
            35                  40                  45
Pro Thr Asp Asp Ile Ser Leu Lys Cys Glu Ala Ser Gly Lys Pro Glu
        50                  55                  60
Val Gln Phe Arg Trp Thr Arg Asp Gly Val His Phe Lys Pro Lys Glu
65                  70                  75                  80
Glu Leu Gly Val Thr Val Tyr Gln Ser Pro His Ser Gly Ser Phe Thr
                85                  90                  95
Ile Thr Gly Asn Asn Ser Asn Phe Ala Gln Arg Phe Gln Gly Ile Tyr
            100                 105                 110
Arg Cys Phe Ala Ser Asn Lys Leu Gly Thr Ala Met Ser His Glu Ile
        115                 120                 125
Arg Leu Met Ala Glu Gly Ala Pro Lys Trp Pro Lys Glu Thr Val Lys
    130                 135                 140
Pro Val Glu Val Glu Glu Gly Glu Ser Val Val Leu Pro Cys Asn Pro
145                 150                 155                 160
Pro Pro Ser Ala Glu Pro Leu Arg Ile Tyr Trp Met Asn Ser Lys Ile
                165                 170                 175
Leu His Ile Lys Gln Asp Glu Arg Val Thr Met Gly Gln Asn Gly Asn
```

```
                  180                 185                 190
Leu Tyr Phe Ala Asn Val Leu Thr Ser Asp A sn His Ser Asp Tyr Ile
        195                 200                 205
Cys His Ala His Phe Pro Gly Thr Arg Thr I le Ile Gln Lys Glu Pro
    210                 215                 220
Ile Asp Leu Arg Val Lys Ala Thr Asn Ser M et Ile Asp Arg Lys Pro
225                 230                 235                 240
Arg Leu Leu Phe Pro Thr Asn Ser Ser Ser H is Leu Val Ala Leu Gln
            245                 250                 255
Gly Gln Pro Leu Val Leu Glu Cys Ile Ala G lu Gly Phe Pro Thr Pro
                260                 265                 270
Thr Ile Lys Trp Leu Arg Pro Ser Gly Pro M et Pro Ala Asp Arg Val
            275                 280                 285
Thr Tyr Gln Asn His Asn Lys Thr Leu Gln L eu Leu Lys Val Gly Glu
        290                 295                 300
Glu Asp Asp Gly Glu Tyr Arg Cys Leu Ala G lu Asn Ser Leu Gly Ser
305                 310                 315                 320
Ala Arg His Ala Tyr Tyr Val Thr Val Glu A la Ala Lys Tyr Arg Ile
                325                 330                 335
Gln Arg Gly Ala Leu Ile Leu Ser Asn Val G ln Pro Ser Asp Thr Met
            340                 345                 350
Val Thr Gln Cys Glu Ala Arg Asn Arg His G ly Leu Leu Leu Ala Asn
        355                 360                 365
Ala Tyr Ile Tyr Val Val Gln Leu Pro Ala L ys Ile Leu Thr Ala Asp
        370                 375                 380
Asn Gln Thr Tyr Met Ala Val Pro Tyr Trp L eu His Lys Pro Gln Ser
385                 390                 395                 400
His Leu Tyr Gly Pro Gly Glu Thr Ala Arg L eu Asp Cys Gln Val Gln
                405                 410                 415
Gly Arg Pro Gln Pro Glu Val Thr Trp Arg I le Asn Gly Ile Pro Val
                420                 425                 430
Glu Glu Leu Ala Lys Asp Gln Gln Gly Ser T hr Ala Tyr Leu Leu Cys
            435                 440                 445
Lys Ala Phe Gly Ala Pro Val Pro Ser Val G ln Trp Leu Asp Glu Asp
    450                 455                 460
Gly Thr Thr Val Leu Gln Asp Glu Arg Phe P he Pro Tyr Ala Asn Gly
465                 470                 475                 480
Thr Leu Gly Ile Arg Asp Leu Gln Ala Asn A sp Thr Gly Arg Tyr Phe
            485                 490                 495
Cys Leu Ala Ala Asn Asp Gln Asn Asn Val T hr Ile Met Ala Asn Leu
        500                 505                 510
Lys Val Lys Asp Ala Thr Gln Ile Thr Gln G ly Pro Arg Ser Thr Ile
    515                 520                 525
Glu Lys Lys Gly Ser Arg Val Thr Phe Thr C ys Gln Ala Ser Phe Asp
    530                 535                 540
Pro Ser Leu Gln Pro Ser Ile Thr Trp Arg G ly Asp Gly Arg Asp Leu
545                 550                 555                 560
Gln Glu Leu Gly Asp Ser Asp Lys Tyr Phe I le Glu Asp Gly Arg Leu
            565                 570                 575
Val Ile His Ser Leu Asp Tyr Ser Asp Gln G ly Asn Tyr Ser Cys Val
        580                 585                 590
Ala Ser Thr Glu Leu Asp Val Val Glu Ser A rg Ala Gln Leu Leu Val
    595                 600                 605
```

Val Gly Ser
    610

(2) INFORMATION FOR SEQ ID NO: 11:

(i) SEQUENCE CHARACTERISTICS:
        (A) LENGTH: 612 amino acids
        (B) TYPE: amino acid
        (D) TOPOLOGY: linear (ii) MOLECULE TYPE: protein (xi) SEQUENCE DESCRIPTION: SEQ ID NO: 11:

Met Met Lys Glu Lys Ser Ile Ser Ala Ser Lys Ala Ser Leu Val Phe
 1               5                  10                  15

Phe Leu Cys Gln Met Ile Ser Ala Leu Asp Val Pro Leu Asp Ser Lys
                20                  25                  30

Leu Leu Glu Glu Leu Ser Gln Pro Pro Thr Ile Thr Gln Gln Ser Pro
            35                  40                  45

Lys Asp Tyr Ile Val Asp Pro Arg Glu Asn Ile Val Ile Gln Cys Glu
 50                  55                  60

Ala Lys Gly Lys Pro Pro Pro Ser Phe Ser Trp Thr Arg Asn Gly Thr
 65                  70                  75                  80

His Phe Asp Ile Asp Lys Asp Ala Gln Val Thr Met Lys Pro Asn Ser
                85                  90                  95

Gly Thr Leu Val Val Asn Ile Met Asn Gly Val Lys Ala Glu Ala Tyr
            100                 105                 110

Glu Gly Val Tyr Gln Cys Thr Ala Arg Asn Glu Arg Gly Ala Ala Ile
            115                 120                 125

Ser Asn Asn Ile Val Ile Arg Pro Ser Arg Ser Pro Leu Trp Thr Lys
130                 135                 140

Glu Lys Leu Glu Pro Asn His Val Arg Glu Gly Asp Ser Leu Val Leu
145                 150                 155                 160

Asn Cys Arg Pro Pro Val Gly Leu Pro Pro Pro Ile Ile Phe Trp Met
                165                 170                 175

Asp Asn Ala Phe Gln Arg Leu Pro Gln Ser Glu Arg Val Ser Gln Gly
            180                 185                 190

Leu Asn Gly Asp Leu Tyr Phe Ser Asn Val Gln Pro Glu Asp Thr Arg
        195                 200                 205

Val Asp Tyr Ile Cys Tyr Ala Arg Phe Asn His Thr Gln Thr Ile Gln
    210                 215                 220

Gln Lys Gln Pro Ile Ser Val Lys Val Phe Ser Thr Lys Pro Val Thr
225                 230                 235                 240

Glu Arg Pro Pro Val Leu Leu Thr Pro Met Gly Ser Thr Ser Asn Lys
                245                 250                 255

Val Glu Leu Arg Gly Asn Val Leu Leu Leu Glu Cys Ile Ala Ala Gly
            260                 265                 270

Leu Pro Thr Pro Val Ile Arg Trp Ile Lys Glu Gly Gly Glu Leu Pro
        275                 280                 285

Ala Asn Arg Thr Phe Phe Glu Asn Phe Lys Lys Thr Leu Lys Ile Ile
    290                 295                 300

Asp Val Ser Glu Ala Asp Ser Gly Asn Tyr Lys Cys Thr Ala Arg Asn
305                 310                 315                 320

Thr Leu Gly Ser Thr His His Val Ile Ser Val Thr Val Lys Ala Ala
                325                 330                 335

```
Pro Tyr Trp Ile Thr Ala Pro Arg Asn Leu Val Leu Ser Pro Gly Glu
            340                 345                 350

Asp Gly Thr Leu Ile Cys Arg Ala Asn Gly Asn Pro Lys Pro Ser Ile
            355                 360                 365

Ser Trp Leu Thr Asn Gly Val Pro Ile Ala Ile Ala Pro Glu Asp Pro
            370                 375                 380

Ser Arg Lys Val Asp Gly Asp Thr Ile Ile Phe Ser Ala Val Gln Glu
385                 390                 395                 400

Arg Ser Ser Ala Val Tyr Gln Cys Asn Ala Ser Asn Glu Tyr Gly Tyr
                    405                 410                 415

Leu Leu Ala Asn Ala Phe Val Asn Val Leu Ala Glu Pro Pro Arg Ile
            420                 425                 430

Leu Thr Pro Ala Asn Lys Leu Tyr Gln Val Ile Ala Asp Ser Pro Ala
            435                 440                 445

Leu Ile Asp Cys Ala Tyr Phe Gly Ser Pro Lys Pro Glu Ile Glu Trp
            450                 455                 460

Phe Arg Gly Val Lys Gly Ser Ile Leu Arg Gly Asn Glu Tyr Val Phe
465                 470                 475                 480

His Asp Asn Gly Thr Leu Glu Ile Pro Val Ala Gln Lys Asp Ser Thr
                    485                 490                 495

Gly Thr Tyr Thr Cys Val Ala Arg Asn Lys Leu Gly Lys Thr Gln Asn
            500                 505                 510

Glu Val Gln Leu Glu Val Lys Asp Pro Thr Met Ile Ile Lys Gln Pro
            515                 520                 525

Gln Tyr Lys Val Ile Gln Arg Ser Ala Gln Ala Ser Phe Glu Cys Val
            530                 535                 540

Ile Lys His Asp Pro Thr Leu Ile Pro Thr Val Ile Trp Leu Lys Asp
545                 550                 555                 560

Asn Asn Glu Leu Pro Asp Asp Glu Arg Phe Leu Val Gly Lys Asp Asn
                    565                 570                 575

Leu Thr Ile Met Asn Val Thr Asp Lys Asp Asp Gly Thr Tyr Thr Cys
            580                 585                 590

Ile Val Asn Thr Thr Leu Asp Ser Val Ser Ala Ser Ala Val Leu Thr
            595                 600                 605

Val Val Ala Ala
610

(2) INFORMATION FOR SEQ ID NO: 12:

(i) SEQUENCE CHARACTERISTICS:
        (A) LENGTH: 607 amino acids
        (B) TYPE: amino acid
        (D) TOPOLOGY: linear (ii) MOLECULE TYPE: protein (xi) SEQUENCE DESCRIPTION: SEQ ID NO: 12:

Met Gly Thr Ala Thr Arg Arg Lys Pro His Leu Leu Leu Val Ala Ala
1               5                   10                  15

Val Ala Leu Val Ser Ser Ser Ala Trp Ser Ser Ala Leu Gly Ser Gln
            20                  25                  30

Thr Thr Phe Gly Pro Val Phe Glu Asp Gln Pro Leu Ser Val Leu Phe
            35                  40                  45

Pro Glu Glu Ser Thr Glu Glu Gln Val Leu Leu Ala Cys Arg Ala Arg
        50                  55                  60

Ala Ser Pro Pro Ala Thr Tyr Arg Trp Lys Met Asn Gly Thr Glu Met
```

```
                65                  70                  75                  80
Lys Leu Glu Pro Gly Ser Arg His Gln Leu V al Gly Gly Asn Leu Val
                    85                  90                  95
Ile Met Asn Pro Thr Lys Ala Gln Asp Ala G ly Val Tyr Gln Cys Leu
                100                 105                 110
Ala Ser Asn Pro Val Gly Thr Val Ser A rg Glu Ala Ile Leu Arg
                115                 120                 125
Phe Gly Phe Leu Gln Glu Phe Ser Lys Glu G lu Arg Asp Pro Val Lys
    130                 135                 140
Ala His Glu Gly Trp Gly Val Met Leu Pro C ys Asn Pro Ala His
145                 150                 155                 160
Tyr Pro Gly Leu Ser Tyr Arg Trp Leu Leu A sn Glu Phe Pro Asn Phe
                165                 170                 175
Ile Pro Thr Asp Gly Arg His Phe Val Ser G ln Thr Thr Gly Asn Leu
                180                 185                 190
Tyr Ile Ala Arg Thr Asn Ala Ser Asp Leu G ly Asn Tyr Ser Cys Leu
                195                 200                 205
Ala Thr Ser His Met Asp Phe Ser Thr Lys S er Val Phe Ser Lys Phe
    210                 215                 220
Ala Gln Leu Asn Leu Ala Ala Glu Asp Thr A rg Leu Phe Ala Pro Ser
225                 230                 235                 240
Ile Lys Ala Arg Phe Pro Ala Glu Thr Tyr A la Leu Val Gly Gln Gln
                245                 250                 255
Val Thr Leu Glu Cys Phe Ala Phe Gly Asn P ro Val Pro Arg Ile Lys
                260                 265                 270
Trp Arg Lys Val Asp Gly Ser Leu Ser Pro G ln Trp Thr Thr Ala Glu
    275                 280                 285
Pro Thr Leu Gln Ile Pro Ser Val Ser Phe G lu Asp Glu Gly Thr Tyr
    290                 295                 300
Glu Cys Glu Ala Glu Asn Ser Lys Gly Arg A sp Thr Val Gln Gly Arg
305                 310                 315                 320
Ile Ile Val Gln Ala Gln Pro Glu Trp Leu L ys Val Ile Ser Asp Thr
                325                 330                 335
Glu Ala Asp Ile Gly Ser Asn Leu Arg Trp G ly Cys Ala Ala Ala Gly
                340                 345                 350
Lys Pro Arg Pro Thr Val Arg Trp Leu Arg A sn Gly Glu Pro Leu Ala
                355                 360                 365
Ser Gln Asn Arg Val Glu Val Leu Ala Gly A sp Leu Arg Phe Ser Lys
    370                 375                 380
Leu Ser Leu Glu Asp Ser Gly Met Tyr Gln C ys Val Ala Glu Asn Lys
385                 390                 395                 400
His Gly Thr Ile Tyr Ala Ser Ala Glu Leu A la Val Gln Ala Leu Ala
                405                 410                 415
Pro Asp Phe Arg Leu Asn Pro Val Arg Arg L eu Ile Pro Ala Ala Arg
                420                 425                 430
Gly Gly Glu Ile Leu Ile Pro Cys Gln Pro A rg Ala Ala Pro Lys Ala
                435                 440                 445
Val Val Leu Trp Ser Lys Gly Thr Glu Ile L eu Val Asn Ser Ser Arg
    450                 455                 460
Val Thr Val Thr Pro Asp Gly Thr Leu Ile I le Arg Asn Ile Ser Arg
465                 470                 475                 480
Ser Asp Glu Gly Lys Tyr Thr Cys Phe Ala G lu Asn Phe Met Gly Lys
                485                 490                 495
```

```
Ala Asn Ser Thr Gly Ile Leu Ser Val Arg Asp Ala Thr Lys Ile Thr
            500                 505                 510

Leu Ala Pro Ser Ser Ala Asp Ile Asn Leu Gly Asp Asn Leu Thr Leu
            515                 520                 525

Gln Cys His Ala Ser His Asp Pro Thr Met Asp Leu Thr Phe Thr Trp
            530                 535                 540

Thr Leu Asp Asp Phe Pro Ile Asp Phe Asp Lys Pro Gly Gly His Tyr
545                 550                 555                 560

Arg Arg Thr Asn Val Lys Glu Thr Ile Gly Asp Leu Thr Ile Leu Asn
            565                 570                 575

Ala Gln Leu Arg His Gly Gly Lys Tyr Thr Cys Met Ala Gln Thr Val
            580                 585                 590

Val Asp Ser Ala Ser Lys Glu Ala Thr Val Leu Val Arg Gly Pro
            595                 600                 605

(2) INFORMATION FOR SEQ ID NO: 13:

(i) SEQUENCE CHARACTERISTICS:
         (A) LENGTH: 596 amino acids
         (B) TYPE: amino acid
         (D) TOPOLOGY: linear (ii) MOLECULE TYPE: protein (xi) SEQUENCE DESCRIPTION: SEQ ID NO: 13:

Met Leu Ser Trp Lys Gln Leu Ile Leu Leu Ser Phe Ile Gly Cys Leu
 1               5                  10                  15

Ala Gly Glu Leu Leu Leu Gln Gly Pro Val Phe Val Lys Glu Pro Ser
            20                  25                  30

Asn Ser Ile Phe Pro Val Gly Ser Glu Asp Lys Lys Ile Thr Leu Asn
            35                  40                  45

Cys Glu Ala Arg Gly Asn Pro Ser Pro His Tyr Arg Trp Gln Leu Asn
        50                  55                  60

Gly Ser Asp Ile Asp Thr Ser Leu Asp His Arg Tyr Lys Leu Asn Gly
 65                 70                  75                  80

Gly Asn Leu Ile Val Ile Asn Pro Asn Arg Asn Trp Asp Thr Gly Ser
            85                  90                  95

Tyr Gln Cys Phe Ala Thr Asn Ser Leu Gly Thr Ile Val Ser Arg Glu
            100                 105                 110

Ala Lys Leu Gln Phe Ala Tyr Leu Glu Asn Phe Lys Ser Arg Met Arg
            115                 120                 125

Ser Arg Val Ser Val Arg Glu Gly Gln Gly Val Val Leu Leu Cys Gly
        130                 135                 140

Pro Pro Pro His Ser Gly Glu Leu Ser Tyr Ala Trp Val Phe Asn Glu
145                 150                 155                 160

Tyr Pro Ser Phe Val Glu Glu Asp Ser Arg Arg Phe Val Ser Gln Glu
            165                 170                 175

Thr Gly His Leu Tyr Ile Ala Lys Val Glu Pro Ser Asp Val Gly Asn
            180                 185                 190

Tyr Thr Cys Val Val Thr Ser Thr Val Thr Asn Ala Arg Val Leu Gly
            195                 200                 205

Ser Pro Thr Pro Leu Val Leu Arg Ser Asp Gly Val Met Gly Glu Tyr
        210                 215                 220

Glu Pro Lys Ile Glu Leu Gln Phe Pro Gly Thr Leu Pro Ala Ala Lys
225                 230                 235                 240
```

```
Gly Ser Thr Val Lys Leu Glu Cys Phe Ala Leu Gly Asn Pro Val Pro
            245                 250                 255

Gln Ile Asn Trp Arg Arg Ser Asp Gly Met Pro Phe Pro Thr Lys Ile
            260                 265                 270

Lys Leu Arg Lys Phe Asn Gly Val Leu Glu Ile Pro Asn Phe Gln Gln
            275                 280                 285

Glu Asp Thr Gly Ser Tyr Glu Cys Ile Ala Glu Asn Ser Arg Gly Lys
        290                 295                 300

Asn Val Ala Arg Gly Arg Leu Thr Tyr Tyr Ala Lys Pro Tyr Trp Val
305                 310                 315                 320

Gln Leu Leu Lys Asp Val Glu Thr Ala Val Glu Asp Ser Leu Tyr Trp
            325                 330                 335

Glu Cys Arg Ala Ser Gly Lys Pro Lys Pro Ser Tyr Arg Trp Leu Lys
            340                 345                 350

Asn Gly Asp Ala Leu Val Leu Glu Glu Arg Ile Gln Ile Glu Asn Gly
            355                 360                 365

Ala Leu Thr Ile Ala Asn Leu Asn Val Ser Asp Ser Gly Met Phe Gln
        370                 375                 380

Cys Ile Ala Glu Asn Lys His Gly Leu Ile Tyr Ser Ser Ala Glu Leu
385                 390                 395                 400

Lys Val Leu Ala Ser Ala Pro Asp Phe Ser Arg Asn Pro Met Lys Lys
            405                 410                 415

Met Ile Gln Val Gln Val Gly Ser Leu Val Ile Leu Asp Cys Lys Pro
            420                 425                 430

Ser Ala Ser Pro Arg Ala Leu Ser Phe Trp Lys Lys Gly Asp Thr Val
            435                 440                 445

Val Arg Glu Gln Ala Arg Ile Ser Leu Leu Asn Asp Gly Gly Leu Lys
            450                 455                 460

Ile Met Asn Val Thr Lys Ala Asp Ala Gly Ile Tyr Thr Cys Ile Ala
465                 470                 475                 480

Glu Asn Gln Phe Gly Lys Ala Asn Gly Thr Thr Gln Leu Val Val Thr
            485                 490                 495

Glu Pro Thr Arg Ile Ile Leu Ala Pro Ser Asn Met Asp Val Ala Val
            500                 505                 510

Gly Glu Ser Ile Ile Leu Pro Cys Gln Val Gln His Asp Pro Leu Leu
            515                 520                 525

Asp Ile Met Phe Ala Trp Tyr Phe Asn Gly Thr Leu Thr Asp Phe Lys
            530                 535                 540

Lys Asp Gly Ser His Phe Glu Lys Val Gly Gly Ser Ser Ser Gly Asp
545                 550                 555                 560

Leu Met Ile Arg Asn Ile Gln Leu Lys His Ser Gly Lys Tyr Val Cys
            565                 570                 575

Met Val Gln Thr Gly Val Asp Ser Val Ser Ser Ala Ala Glu Leu Ile
            580                 585                 590

Val Arg Gly Ser
        595

(2) INFORMATION FOR SEQ ID NO: 14:

(i) SEQUENCE CHARACTERISTICS:
        (A) LENGTH: 630 amino acids
        (B) TYPE: amino acid
        (D) TOPOLOGY: linear (ii) MOLECULE TYPE: protein
```

-continued (xi) SEQUENCE DESCRIPTION: SEQ ID NO: 14:

Met Val Leu His Ser His Gln Leu Thr Tyr Ala Gly Ile Ala Phe Ala
1               5                   10                  15

Leu Cys Leu His His Leu Ile Ser Ala Ile Glu Val Pro Leu Asp Ser
            20                  25                  30

Asn Ile Gln Ser Glu Leu Pro Gln Pro Pro Thr Ile Thr Lys Gln Ser
        35                  40                  45

Val Lys Asp Tyr Ile Val Asp Pro Arg Asp Asn Ile Phe Ile Glu Cys
    50                  55                  60

Glu Ala Lys Gly Asn Pro Val Pro Thr Phe Ser Trp Thr Arg Asn Gly
65                  70                  75                  80

Lys Phe Phe Asn Val Ala Lys Asp Pro Lys Val Ser Met Arg Arg Arg
                85                  90                  95

Ser Gly Thr Leu Val Ile Asp Phe His Gly Gly Arg Pro Asp Asp
            100                 105                 110

Tyr Glu Gly Glu Tyr Gln Cys Phe Ala Arg Asn Asp Tyr Gly Thr Ala
        115                 120                 125

Leu Ser Ser Lys Ile His Leu Gln Val Ser Arg Ser Pro Leu Trp Pro
    130                 135                 140

Lys Glu Lys Val Asp Val Ile Glu Val Asp Glu Gly Ala Pro Leu Ser
145                 150                 155                 160

Leu Gln Cys Asn Pro Pro Gly Leu Pro Pro Pro Val Ile Phe Trp
                165                 170                 175

Met Ser Ser Ser Met Glu Pro Ile His Gln Asp Lys Arg Val Ser Gln
            180                 185                 190

Gly Gln Asn Gly Asp Leu Tyr Phe Ser Asn Val Met Leu Gln Asp Ala
        195                 200                 205

Gln Thr Asp Tyr Ser Cys Asn Ala Arg Phe His Phe Thr His Thr Ile
    210                 215                 220

Gln Gln Lys Asn Pro Tyr Thr Leu Lys Val Lys Thr Lys Pro His
225                 230                 235                 240

Asn Glu Thr Ser Leu Arg Asn His Thr Asp Met Tyr Ser Ala Arg Gly
            245                 250                 255

Val Thr Glu Thr Thr Pro Ser Phe Met Tyr Pro Tyr Gly Thr Ser Ser
        260                 265                 270

Ser Gln Met Val Leu Arg Gly Val Asp Leu Leu Leu Glu Cys Ile Ala
    275                 280                 285

Ser Gly Val Pro Ala Pro Asp Ile Met Trp Tyr Lys Lys Gly Gly Glu
290                 295                 300

Leu Pro Ala Gly Lys Thr Lys Leu Glu Asn Phe Asn Lys Ala Leu Arg
305                 310                 315                 320

Ile Ser Asn Val Ser Glu Glu Asp Ser Gly Glu Tyr Phe Cys Leu Ala
            325                 330                 335

Ser Asn Lys Met Gly Ser Ile Arg His Thr Ile Ser Val Arg Val Lys
        340                 345                 350

Ala Ala Pro Tyr Trp Leu Asp Glu Pro Gln Asn Leu Ile Leu Ala Pro
    355                 360                 365

Gly Glu Asp Gly Arg Leu Val Cys Arg Ala Asn Gly Asn Pro Lys Pro
370                 375                 380

Ser Ile Gln Trp Leu Val Asn Gly Glu Pro Ile Glu Gly Ser Pro Pro
385                 390                 395                 400

Asn Pro Ser Arg Glu Val Ala Gly Asp Thr Ile Val Phe Arg Asp Thr
            405                 410                 415

-continued

```
Gln Ile Gly Ser Ser Ala Val Tyr Gln Cys Asn Ala Ser Asn Glu His
            420                 425                 430
Gly Tyr Leu Leu Ala Asn Ala Phe Val Ser Val Leu Asp Val Pro Pro
            435                 440                 445
Arg Ile Leu Ala Pro Arg Asn Gln Leu Ile Lys Val Ile Gln Tyr Asn
    450                 455                 460
Arg Thr Arg Leu Asp Cys Pro Phe Phe Gly Ser Pro Ile Pro Thr Leu
465                 470                 475                 480
Arg Trp Phe Lys Asn Gly Gln Gly Asn Met Leu Asp Gly Gly Asn Tyr
                485                 490                 495
Lys Ala His Glu Asn Gly Ser Leu Glu Met Ser Met Ala Arg Lys Glu
            500                 505                 510
Asp Gln Gly Ile Tyr Thr Cys Val Ala Thr Asn Ile Leu Gly Lys Val
            515                 520                 525
Glu Ala Gln Val Arg Leu Glu Val Lys Asp Pro Thr Arg Ile Val Arg
530                 535                 540
Gly Pro Glu Asp Gln Val Val Lys Arg Gly Ser Met Pro Arg Leu His
545                 550                 555                 560
Cys Arg Val Lys His Asp Pro Thr Leu Lys Leu Thr Val Thr Trp Leu
                565                 570                 575
Lys Asp Asp Ala Pro Leu Tyr Ile Gly Asn Arg Met Lys Lys Glu Asp
                580                 585                 590
Asp Gly Leu Thr Ile Tyr Gly Val Ala Glu Lys Asp Gln Gly Asp Tyr
            595                 600                 605
Thr Cys Val Ala Ser Thr Glu Leu Asp Lys Asp Ser Ala Lys Ala Tyr
    610                 615                 620
Leu Thr Val Leu Ala Ile
625                 630
```